United States Patent
Krause et al.

(10) Patent No.: US 9,050,123 B2
(45) Date of Patent: Jun. 9, 2015

(54) POWERED SURGICAL SYSTEM

(75) Inventors: Kenneth W. Krause, Sandown, NH (US); Kenneth R. Woodland, Wilmington, MA (US); Michael S. Garcia, Chelmsford, MA (US); Michael A. Brodsky, Hillsboro, NH (US); Uday Hegde, Acton, MA (US); Melanie Meier, Windham, NH (US); Elangovan Ramanathan, Saco, ME (US)

(73) Assignee: Smith & Nephew, Inc., Memphis, TN (US)

( * ) Notice: Subject to any disclaimer, the term of this patent is extended or adjusted under 35 U.S.C. 154(b) by 1442 days.

(21) Appl. No.: 12/104,286

(22) Filed: Apr. 16, 2008

(65) Prior Publication Data
US 2008/0262476 A1    Oct. 23, 2008

Related U.S. Application Data

(60) Provisional application No. 60/912,067, filed on Apr. 16, 2007.

(51) Int. Cl.
*A61B 18/18*    (2006.01)
*A61B 17/32*    (2006.01)
(Continued)

(52) U.S. Cl.
CPC ... *A61B 17/32002* (2013.01); *A61B 17/320783* (2013.01); *A61B 2017/00017* (2013.01);
(Continued)

(58) Field of Classification Search
CPC ............... A61B 17/32002; A61B 17/302783; A61B 2017/00017; A61B 2017/00137; A61B 2017/0019; A61B 2017/00199; A61B 2017/00225; A61B 2017/00973; A61B 2017/00977; A61B 2018/301; A61B 18/10; A61B 18/12; A61B 18/1206; A61B 12/10; A61B 12/1233; A61B 18/1442; A61B 2018/00005; A61B 2018/00053; A61B 2018/00315; A61B 2018/00565; A61B 2018/00577; A61B 2018/00636; A61B 2018/0091; A61B 2018/00964; A61B 2018/00988; A61B 2018/00642; A61B 2018/00702; A61B 2018/00875; A61B 2218/002; A61B 2218/007
USPC ........................................................ 606/32–35
See application file for complete search history.

(56) References Cited

U.S. PATENT DOCUMENTS 5,602,449 A * 2/1997 Krause et al. ............ 318/400.09
5,669,921 A   9/1997 Berman et al.
(Continued)

FOREIGN PATENT DOCUMENTS

JP    5337126 A    12/1993
JP    2004500187 A    1/2004
(Continued)

OTHER PUBLICATIONS

International Search Report and Written Opinion for International Application No. PCT/US2008/060469, mailed Dec. 9, 2008, 19 pages.
(Continued)

*Primary Examiner* — Joseph Stoklosa
*Assistant Examiner* — Amanda Scott
(74) *Attorney, Agent, or Firm* — Chapin IP Law, LLC

(57) ABSTRACT

A system for treating tissue includes a device including a first member and a second member arranged to move relative to the first member to treat tissue. The system also includes a processor configured to automatically control movement of the second member relative to the first member using position control methodology. A method of treating tissue includes providing a device having a first member and a second member arranged to move relative to the first member, moving the second member relative to the first member, and automatically controlling the movement of the second member using position control methodology.

13 Claims, 16 Drawing Sheets

(51) Int. Cl.
  *A61B 17/3207* (2006.01)
  *A61B 17/00* (2006.01)
  *A61B 19/00* (2006.01)

(52) U.S. Cl.
  CPC .......... *A61B2017/00137* (2013.01); *A61B 2017/0019* (2013.01); *A61B 2017/00199* (2013.01); *A61B 2017/00225* (2013.01); *A61B 2017/00973* (2013.01); *A61B 2017/00977* (2013.01); *A61B 2019/301* (2013.01)

(56) References Cited

U.S. PATENT DOCUMENTS

| | | |
|---|---|---|
| 5,733,298 A | 3/1998 | Berman et al. |
| 6,245,084 B1 | 6/2001 | Mark et al. |
| 6,428,487 B1 | 8/2002 | Burdorff et al. |
| 6,723,106 B1 | 4/2004 | Charles et al. |
| 2006/0074405 A1 | 4/2006 | Malackowski et al. |
| 2007/0085496 A1 | 4/2007 | Philipp et al. |

FOREIGN PATENT DOCUMENTS

| | | |
|---|---|---|
| JP | 2004280605 A | 10/2004 |
| WO | WO 95/03001 | 2/1995 |
| WO | WO0030557 A1 | 6/2000 |
| WO | WO0154558 A8 | 10/2002 |
| WO | WO2006011119 A1 | 2/2006 |

OTHER PUBLICATIONS

Invitation to Pay Additional Fees and Partial Search Report for International Application No. PCT/US2008/060469, mailed Aug. 4, 2008, 6 pages.

Notice of Reasons for Rejection for Japanese Application No. 2010-504213, mailed Jan. 29, 2013.

Patent Examination Report No. 1 for Australian Application No. 2008242981, mailed Aug. 23, 2012.

\* cited by examiner

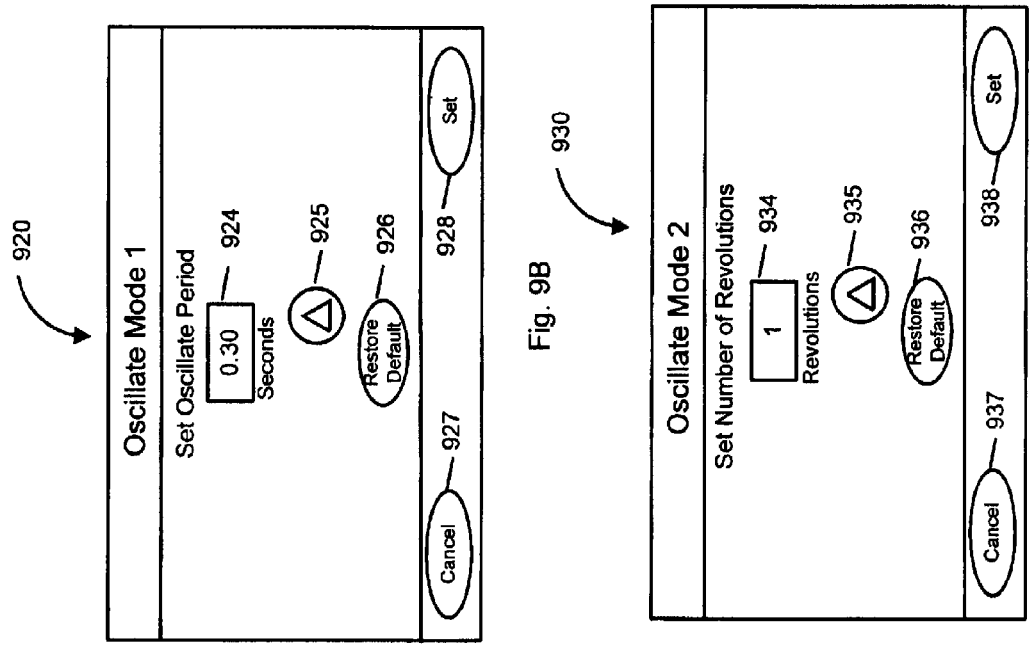
Fig. 9B
Fig. 9C
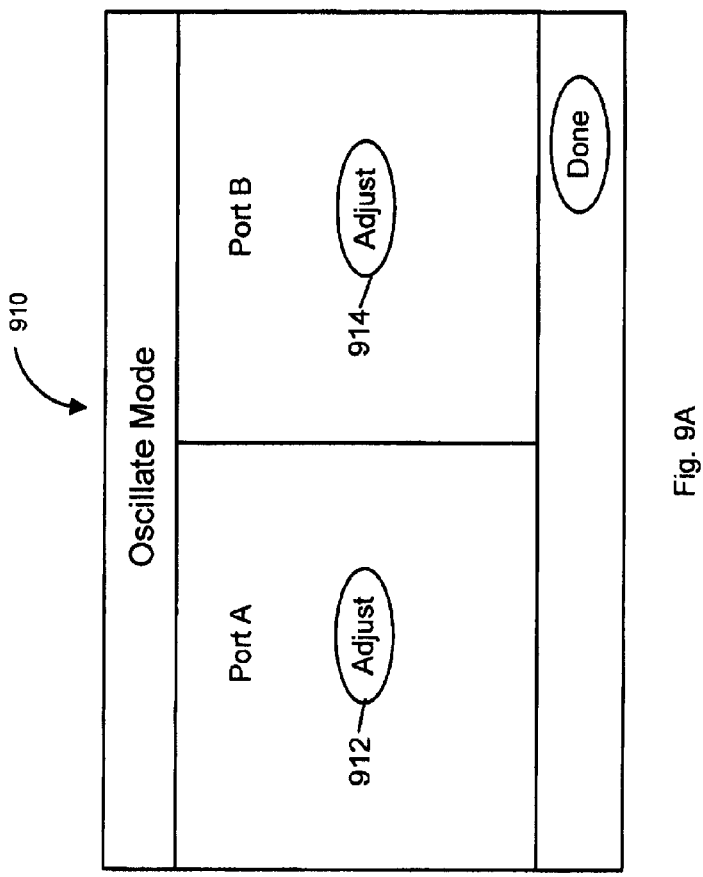
Fig. 9A

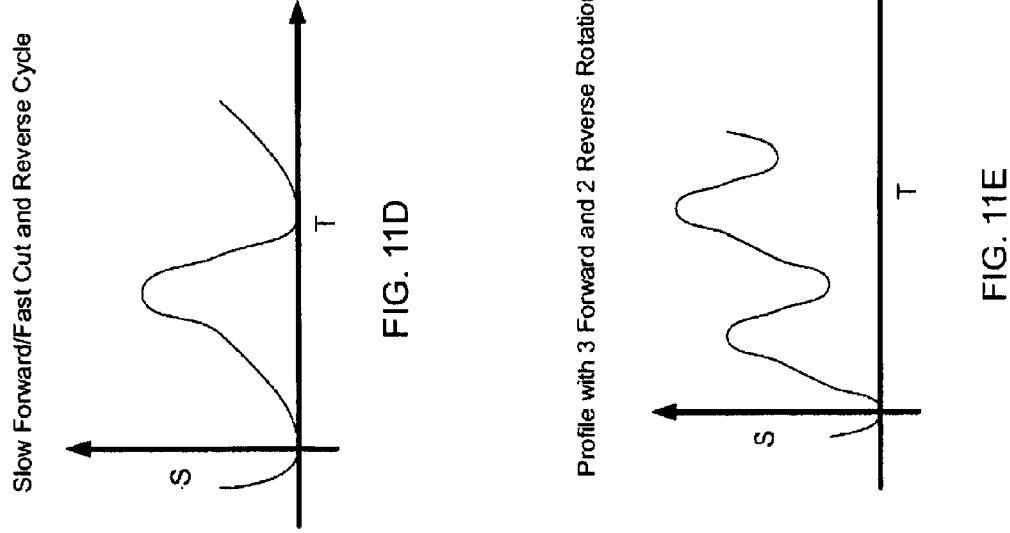
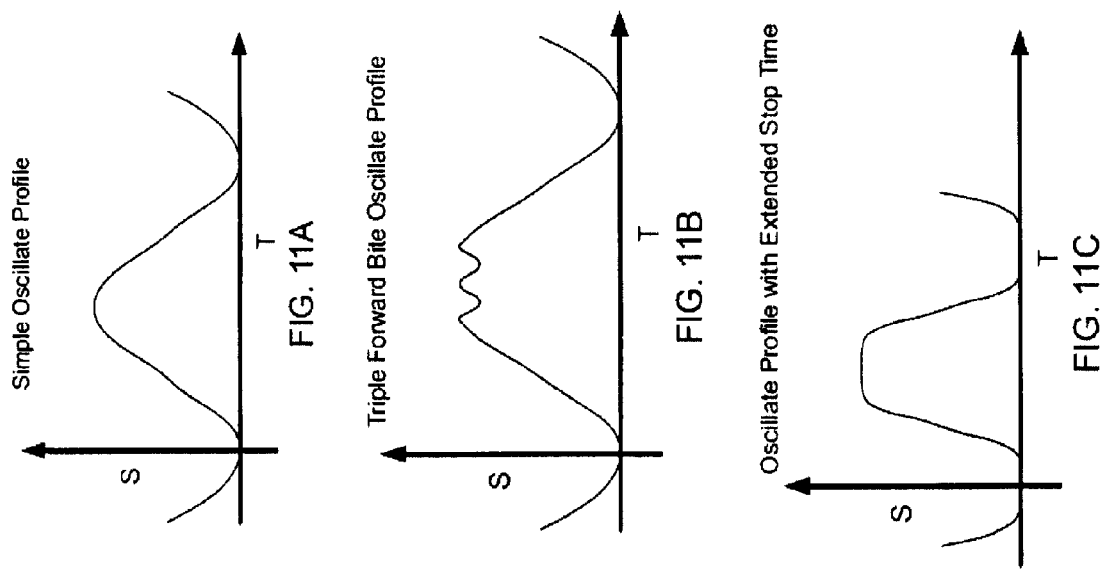

POWERED SURGICAL SYSTEM

CROSS-REFERENCE TO RELATED APPLICATIONS

This application claims the benefit of U.S. Provisional Application No. 60/912,067, filed on Apr. 16, 2007, which is incorporated herein by reference in its entirety.

TECHNICAL FIELD

This invention relates to a powered surgical system.

BACKGROUND

Powered surgical systems typically include a console and associated surgical instruments. The console powers and controls the instruments. The instruments typically include motorized instruments used in surgical procedures such as functional endoscopic sinus surgery, arthroscopy procedures, and the resection of soft and osseous tissues.

SUMMARY

In one general implementation, a system for treating tissue includes a device that includes a first member and a second member arranged to move relative to the first member to treat tissue. The system also includes a processor configured to automatically control movement of the second member relative to the first member using position control methodology.

Implementations can include one or more of the following features. For example, the processor controls movement of the second member relative to the first member such that there is a hold period at least at some occurrences of the aperture being in fluid communication with the tissue environment. The processor computes acceleration and deceleration needed to move the second member between points of a position profile. Each point of the position profile corresponds to a position where the aperture of the device is in fluid communication with the tissue environment. The second member rotates relative to the first member or reciprocates axially relative to the first member. The position control methodology uses a stop position of the second member to compute acceleration or deceleration needed to move between points of a position profile. The position control methodology uses a point of shaft reversal of the second member to compute acceleration or deceleration needed to move between points of a position profile. The first and second members cooperatively define an aperture in the device which depending upon the position of the second member relative to the first member is in fluid communication or is out of fluid communication with a tissue environment.

In another general aspect, a method of treating tissue includes providing a device having a first member and a second member arranged to move relative to the first member, moving the second member relative to the first member, and automatically controlling the movement of the second member using position control methodology.

Implementations can include one or more of the following features. For example, moving the second member relative to the first member alternately places an aspiration opening of the device into fluid communication with or out of fluid communication with a tissue environment. The second member is automatically controlled such that there is a hold period at least at some occurrences of the aspiration opening being in fluid communication with the tissue environment. Automatically controlling the movement of the second member includes computing acceleration and deceleration needed to move the second member between points of a position profile. Each point of the position profile corresponds to a position where the aspiration opening of the device is in fluid communication with the tissue environment. Moving the second member relative to the first member includes rotating the second member relative to the first member. Automatically controlling the movement of the second member includes accelerating and decelerating the second member to cause two rotations of the second member relative to the first member, and then reversing the direction of rotation of the second member. The second member is automatically controlled such that the second member is slowed down or stopped when the aspiration opening is in fluid communication with the tissue environment. Moving the second member relative to the first member includes reciprocating the second member axially relative to the first member. Automatically controlling the movement of the second member using position control methodology includes using a stop position or point of shaft reversal of the second member to compute acceleration or deceleration needed to move between points of a position profile.

In another general implementation, a powered surgical system includes a main control unit including a display, a footswitch connection port, and an instrument port for operation of a surgical instrument device, a power supply housed within the main control unit, and a processor housed within the main control unit and enabling multiple, user-selectable oscillation profiles. The user-selectable oscillation profiles include a velocity controlled mode in which motor speed of a surgical instrument is ramped from zero to a target speed, then back to zero, in a period of time, at which time the direction is reversed, and a position controlled mode in which the motor speed accelerates and decelerates to cause a number of revolutions of the surgical instrument, at which position the direction is reversed.

Implementations can include one or more of the following features. For example, motor speed accelerates and decelerates to cause two revolutions of the surgical instrument, at which position the direction is reversed. The main control unit includes two instrument ports and two footswitch connections ports for simultaneous operation of two instruments. The system can include two instruments connected to the two instrument ports and two footswitches connected to the footswitch connection ports. The two instruments and the footswitches are configurable to communicate configuration, sensory and control data to the main control unit via wired or wireless links. A user interface is configured to receive user-selectable data for controlling operation of the surgical instrument and to display operational parameters associated with the surgical instrument. The wired link includes a bi-directional RS-485 connection or other wired connection. The wireless link includes a Bluetooth connection or other wireless protocol. The system further includes an electro-surgical power generator for providing power to one or more surgical handpieces connectable to the generator.

In another general implementation, a surgical assembly includes a control unit, intelligent peripherals capable of communicating configuration, sensory, and control data to the control unit via wired or wireless links, and a processor housed within the control unit. The processor is configured to enable multiple, user-selectable oscillation profiles including a position controlled mode in which the processor calculates the acceleration or deceleration to move between points of a position profile.

Implementations can include one or more of the following features. For example, an intelligent peripheral includes a motor drive unit configured to communicate position profile data optimized for the geometry of a surgical blade attached thereto. The control unit includes two instrument ports and two footswitch connection ports for simultaneous operation of two surgical instruments.

In another general implementation, a method for controlling movement of a motor shaft based on an algorithm that includes a position profile defining multiple positions of the motor shaft over a period of time includes providing a device having a first member and a second member, the second member coupled to the motor shaft and arranged to move relative to the first member, and moving the motor shaft, which, in turn, moves the second member relative to the first member, between the multiple positions of the position profile within the period of time.

Implementations can include one or more of the following features. For example, the method includes determining the acceleration or deceleration to move the motor shaft between the positions of the position profile. When the second member is moved to each of the multiple positions of the position profile, an aspiration opening cooperatively defined by the first and second members is in fluid communication with a tissue environment. Moving the motor shaft includes controlling electrical power to the motor shaft based on a target shaft position and an actual shaft position. Controlling electrical power includes inputting the target shaft position and the actual shaft position to a discrete-time proportional-integral-derivative (PID) controller. The method can be performed such that there is a hold period at least at some of the positions of the position profile.

In another general implementation, a surgical system includes a console, a universal drive housed within the console and configured for one or more phase motor control, and a processor housed within the console and enabling multiple, user-selectable oscillation profiles including: a velocity controlled mode in which motor speed of a device is ramped from zero to a target speed, then back to zero, in a period of time, at which time the direction in reversed; and a position controlled mode in which the motor speed accelerates and decelerates to cause a number of revolutions of the device, at which position the direction is reversed.

DESCRIPTION OF THE DRAWINGS

FIGS. 9A-9C are illustrations of settings screens of the console of FIG. 2A.

FIGS. 11A-11E illustrate position profiles for a blade of an instrument.

DETAILED DESCRIPTION

Figure 1:
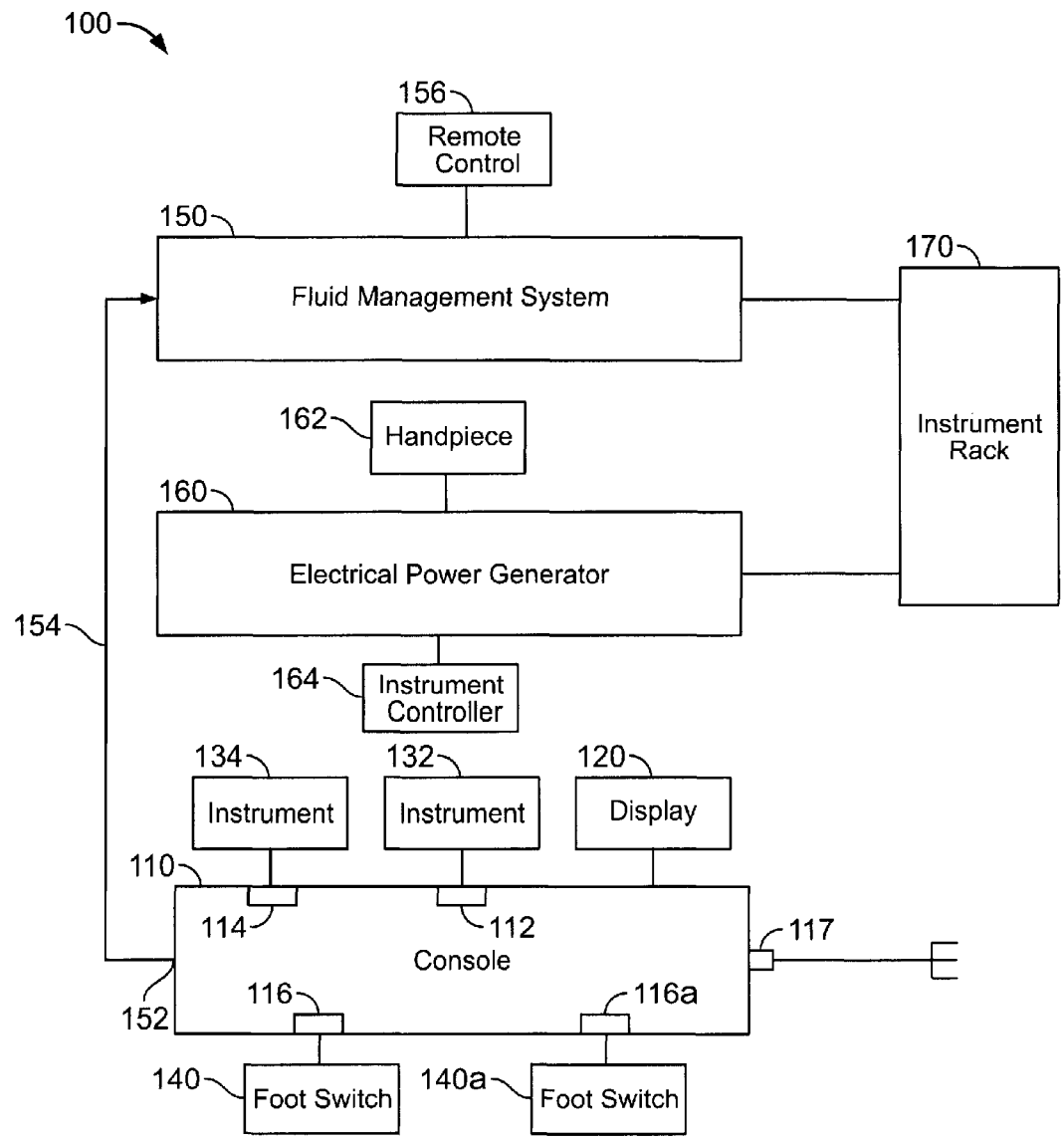
FIG. 1 is an illustration of a surgical system.

Referring to FIG. 1, a surgical system 100 includes a console 110, one or more instruments 132, 134 driven by the console 110, a fluid management system, such as pump 150 that provides pressure during surgical procedures, an electrosurgical generator 160 that powers handpieces used in, for example, temperature control, cutting, and ablation applications, and an instrument rack 170.

The console 110 includes two instrument ports 112 and 114, to which instruments 132 and 134 are respectively connected. The instruments 132 and 134 can include motor drive units and powered arthroscopic instruments, such as drills, wire/pin drivers, and sagittal saws. These instruments are used in, the resection of soft and osseous tissues in large and small articular cavities, for example. The instruments also can be used in Functional Endoscopic Sinus Surgery (FESS). The console 110 allows for simultaneous use and control of the instruments 132, 134. The instruments 132 and 134 can include two motor drive units, two powered instruments, or a combination of a motor drive unit and powered instrument. The instrument port 112 and the instrument port 114 are also respectively referred to as "Port A" and "Port B."

As described in more detail below, the console 110 permits a user to manage the movement of one or more instruments connected to the console 110 via a user-programmable oscillation mode algorithm. The console 110 supports two oscillation modes: (1) a velocity-controlled mode in which motor speed is ramped from zero to a specified target speed and then ramped from the target speed to zero again in a specified time; and (2) a position-controlled mode in which the motor accelerates and decelerates to specified positions in specified periods of time to enable reversal of direction to return to a starting position. The position control methodology provides enhanced system precision and flexibility because rather than using shaft position to signal (trigger) a control algorithm when to stop or reverse direction (e.g., a velocity control algorithm), shaft position is the input to a position control algorithm. Thus, the stop position or point of shaft reversal is known in advance by the control algorithm as it computes the acceleration or deceleration to move between the points of the position profile.

The console 110 also includes a footswitch connection port 116 to which a footswitch 140 is connected. The footswitch 140 is configured to drive either of the instruments 132 and 134. In further implementations, the console 110 can include an additional footswitch connection port 116a to which an additional footswitch 140a is connected. The footswitch 140a can be configured to drive either of the other of the instruments 132 and 134. As discussed in greater detail with respect to FIGS. 5, 8, 9, and 13, the console 110 also displays user prompts and system diagnostic text on a liquid crystal display (LCD) 120. The console 110 also includes a port 117 through which the console 110 is connected to a power source, such as a wall receptacle at 120 volts AC, 15 A, and 50-60 Hz, or other voltages.

As discussed in more detail below, the console 110 provides support for intelligent peripherals, such as the instruments 132 and 134 and the footswitch 140. The instruments 132 and 134 and the footswitch 140 communicate configuration, sensory, and control data to the console 110 via the ports 112, 114, and 116, respectively. The instruments 132 and 134 can be connected to the ports 112 and 114 via wired links. The footswitch 140 can be connected to the port 116 via wired or wireless links. The ports 112, 114, and 116 can be bi-directional RS-485 connections. The port 116 can also be a Bluetooth or other wireless protocol connection. All of the ports 112, 114, and 116 can be the same type of port (e.g., all RS-485), or the ports 112, 114, and 116 can be different types of ports (e.g., the 112 and 114 ports can both be RS-485 ports and the port 116 can be a Bluetooth or other wireless protocol port). The peripherals can be "plug-in-play" such that they can communicate certain data, such as position profile data to the console 110 once they are connected to one of the ports 112, 114.

The pump 150 is connected to the console 110 through a bi-directional port 152 on the console 110. The pump 150 optionally includes a remote control 156, which can be used to control operation of the pump 150 (e.g., select pressure settings) during surgical applications. An exemplary pump 150 for use in the system 100 is a DYONICS 25 Fluid Management System Control Unit, available from Smith & Nephew, Inc. The pump 150 is connected to the instrument rack 170, an example of which is a Procedure Cart with Transformer available from Smith & Nephew, Inc.

The electro-surgical generator 160 is also coupled to the instrument rack 170 and to a handpiece 162. The handpiece 162 is, for example, a single-use or multi-use probe for temperature control, cutting, or ablation that emits radio-frequency radiation generated by the electro-surgical generator 160. The handpiece 162 includes integrated cables (not shown) and uses autoprobe recognition to determine the type of probe connected to the handpiece 162. The electro-surgical generator 160 is also connected to an instrument controller 164, an example of which is a footswitch used to control the amount of radiation emitted from the handpiece 162.

Figure 2A:
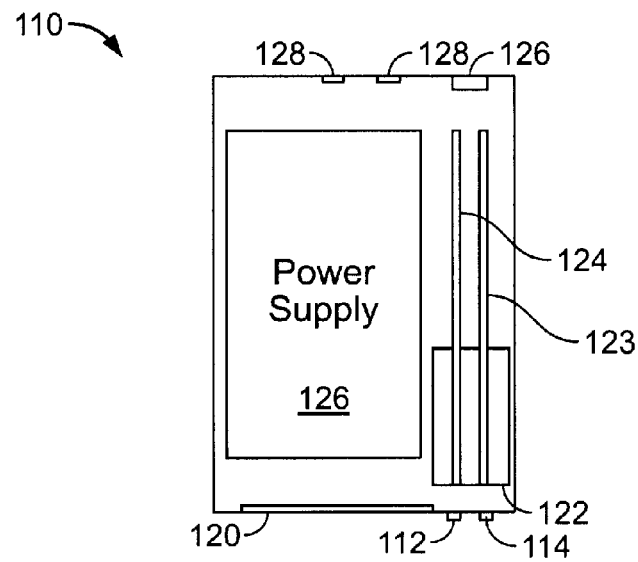
FIG. 2A is a schematic illustration of a console of the system of FIG. 1.

Referring to FIG. 2A, the console 110 includes a display 120, instrument ports 112 and 114, a connector board 122, a motor controller board 123, a system controller board 124, network interfaces 126, and serial ports 128. The console 110 is a software-configurable universal-drive platform that allows simultaneous operation of the motors of two to four or more instruments connected to the console 110. The motors can be, for example, one-third horsepower and one- to four or higher-phase DC motors. The display 120 is a touch screen liquid crystal display that displays an interface and controls used to set up and operate the console 110. As discussed in more detail with respect to FIGS. 5, 8, 9, and 13, the interface and controls allow adjustment of settings in the console 110, such as adjustment of an operating speed of an instrument attached to the console 110 and selection of oscillation modes for the instruments 132 and 134. The display 120 also displays system controls, system information, and procedure information. The instrument ports 112, 114, and 116 are configured to receive peripheral devices, such as the instruments 132 and 134, and the footswitch 140. The instrument ports 112, 114, and 116 are configured for analog and digital inputs and can include an RS-485 or other wired interface. Instrument port 116 can alternatively include a Bluetooth interface or other wireless interface.

The connector board 122 includes interfaces configured to receive circuit boards, such as the motor controller board 123 and the system controller board 124. The motor controller board 123 is a generic slave dual motor controller within a distributed platform, but can include other controllers, such as electro-surgical controllers or other types of motor controller boards. The motor controller board 123 includes a processor, memory, software, and motor drive circuitry. The motor controller board 123 buffers external inputs for use by application software running on the system controller board 124. The application software sends commands to the motor controller board 123 to control the functionality of motors in instruments connected to the console 110, such as a motor in each of the instruments 132 and 134. Multiple controller boards 123 could be employed, along with multiple instrument ports on the console 110 to accommodate, for example, up to four or more independently controlled instruments, such as instruments 132 and 134.

The system controller board 124, in conjunction with the motor controller board 123, controls the motors in the instruments 132, 134 connected to the console 110, by communicating control and parametric data bi-directionally with the motor controller board 123. The system controller board 124 includes a processor, an operating system, and application software. As discussed in more detail below, a controlling application on the system controller board 124 in conjunction with the display 120 provides graphical status indicators and touch screen control over the motor operation. The system controller board 124 also provides status signals to the pump 150 in implementations in which the pump 150 is connected to the console 110. The system controller board 124 also provides status signals to digital control systems, such as Smith & Nephew Inc.'s CONDOR™ control system and can receive control signals from such digital control systems. These digital control systems enable users to send commands to, for example, instruments 132, 134, and other medical devices, digital cameras, image management systems and other components using voice commands and a wireless touch panel. The systems also enable real-time streaming audio and video of the procedure over the Internet to classrooms, offices and consulting surgeons in other locations.

Figure 2B:
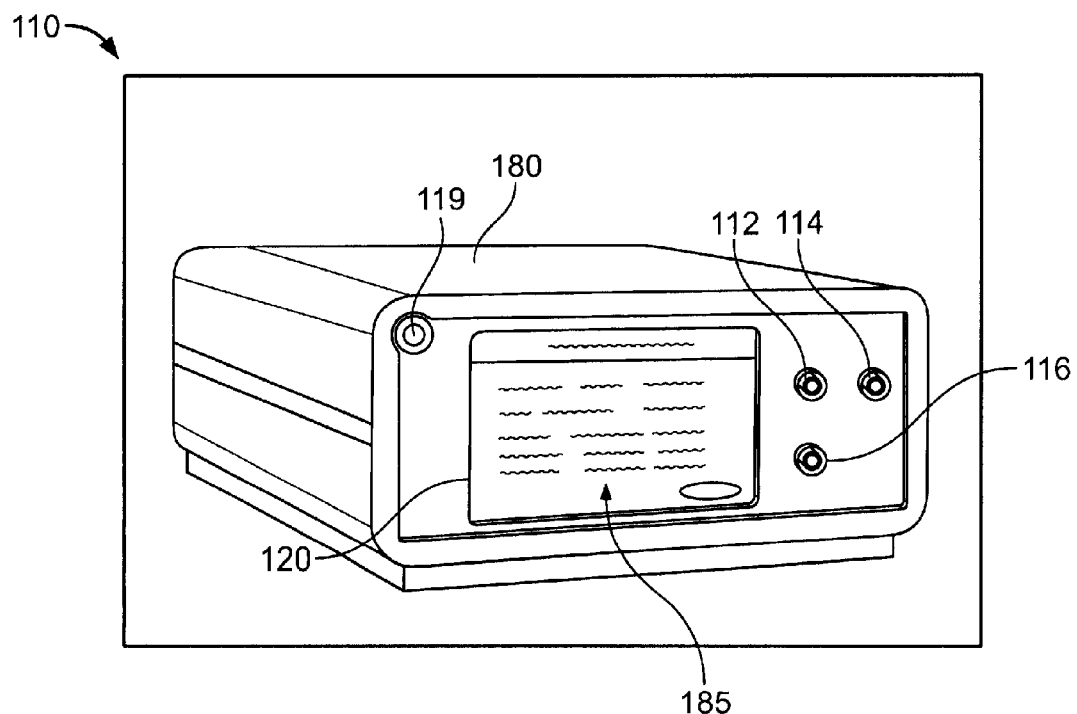
FIG. 2B is a front perspective view of the console of FIG. 2A.
Figure 2C:
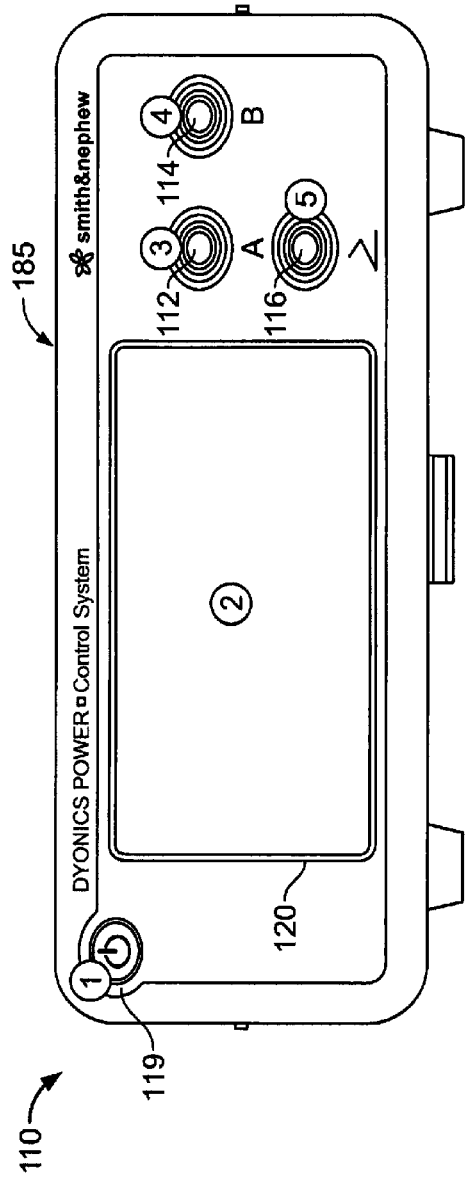
FIG. 2C is a front view of the console of FIG. 2A.
Figure 2D:
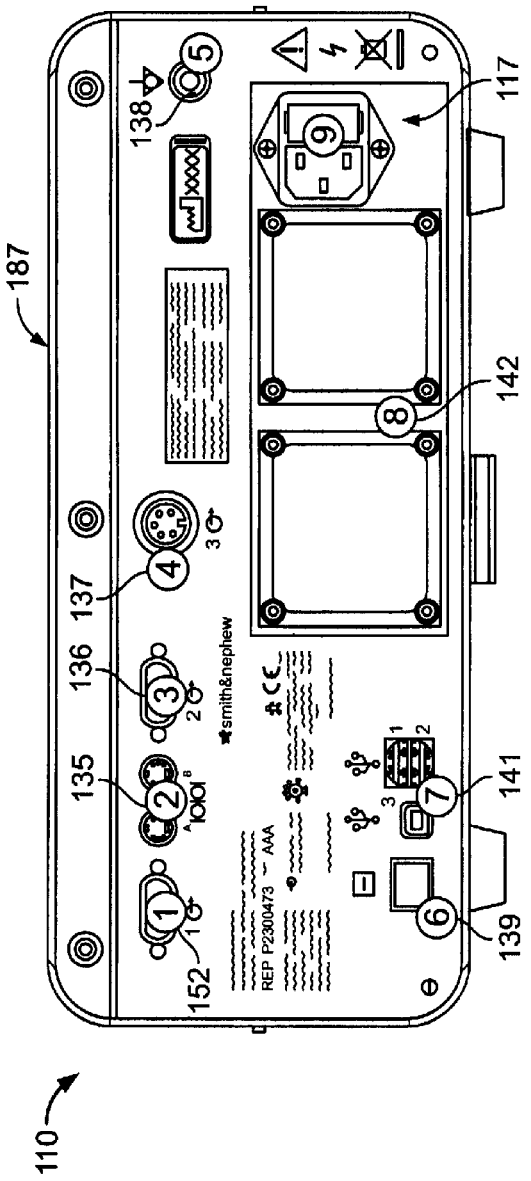
FIG. 2D is a rear view of the console of FIG. 2A.

Referring to FIGS. 2B and 2C, the console 110 is enclosed in a housing 180. A front panel 185 of the housing 180 includes the display 120, the instrument ports 112 and 114, the footswitch connection port 116, and a power switch 119. The power switch 119 initiates procedures to power the console 110 (e.g., turn the console 110 on) and to remove power from the console 110 (e.g., turn the console 110 off). As shown in FIG. 2D, the housing 180 includes a rear panel 187. The rear panel 187 includes the bi-directional port 152, serial ports 135, a second bi-directional port 136, a third bi-directional port 137, a case ground 138, a network interface 139, field programmable ports 141, exhaust fans 142, and the power connector 117. The bidirectional port 152 connects the console 110 to a fluid management system, such as the pump 150 discussed above with respect to FIG. 1. The second bi-directional port 136 connects the console 110 to a digital operating room control center. The case ground 138 is connected to equipment within or external to the console 110 to bring the equipment to the same electrical ground as the housing 180. The exhaust fans 142 provide cooling for the console 110, and the power connector 117 allows the console 110 to be connected to a hospital-grade power cord accessory (not shown). The power connector 117 is an integral part of the console 110 and is configured as a receptacle that accommodates the power cord accessory.

Figure 3:
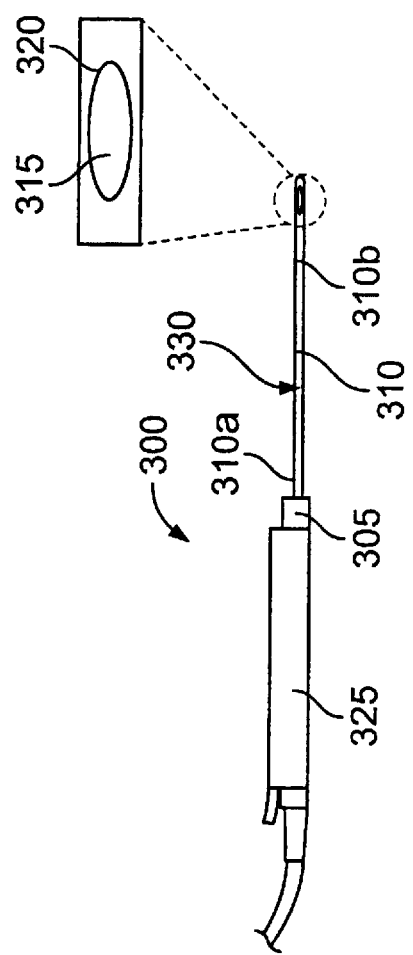
FIG. 3 is a side perspective view of a surgical instrument.

FIG. 3 illustrates an exemplary surgical device 300 used in conjunction with the console 110. Surgical device 300 uses a tube-in-tube construction to shear tissue disposed between cutting edges of an elongate outer non-rotating tubular member 310 and an elongate inner rotating tubular member 315, as more fully explained in, for example, U.S. Pat. No. 5,871,493, which is incorporated herein by reference in its entirety. The surgical device 300 includes a MDU 325 coupled to the members 310, 315 at an interface 305. The outer tubular member 310 has a proximal end 310a coupled to the interface 305 and a distal end 310b defining an opening 320 forming a cutting port or window. The inner tubular member 315 is rotatably received in the outer tubular member 310 and has a cutting edge (not shown) at its distal end. The inner tubular member 315 defines an aspiration lumen (not shown) communicating with the cutting edge to remove cut tissue and fluid from a surgical site. When the surgical device 300 is assembled, the cutting edge of the inner tubular member 315 is positioned adjacent the opening 320 of the outer tubular member 310 and aligns with the opening 320 such that during certain portions of the rotation of the inner member 315 with respect to the outer member 310 the opening 320 and the aspiration lumen are either in fluid communication or is out of fluid communication with a tissue environment.

The surgical device 300 is connected to either the instrument port 112 (port A) or the instrument port 114 (port B) on the front panel 185 of the console 110. Once connected to either port 112, 114, the console 110 automatically detects the presence of the surgical device 300. A variety of disposable straight and curved surgical blades and burrs 330 can be inserted into the surgical device 300 at the interface 305 for various surgical applications. Action of the inner member 315 is controlled by either the instrument or a footswitch, selecting forward, reverse or oscillate. As will be described in more detail below, the console 110 provides user-selectable settings for blade speed within minimum and maximum speeds, with the minimum and maximum speeds preprogrammed for each blade type.

Figure 3A:
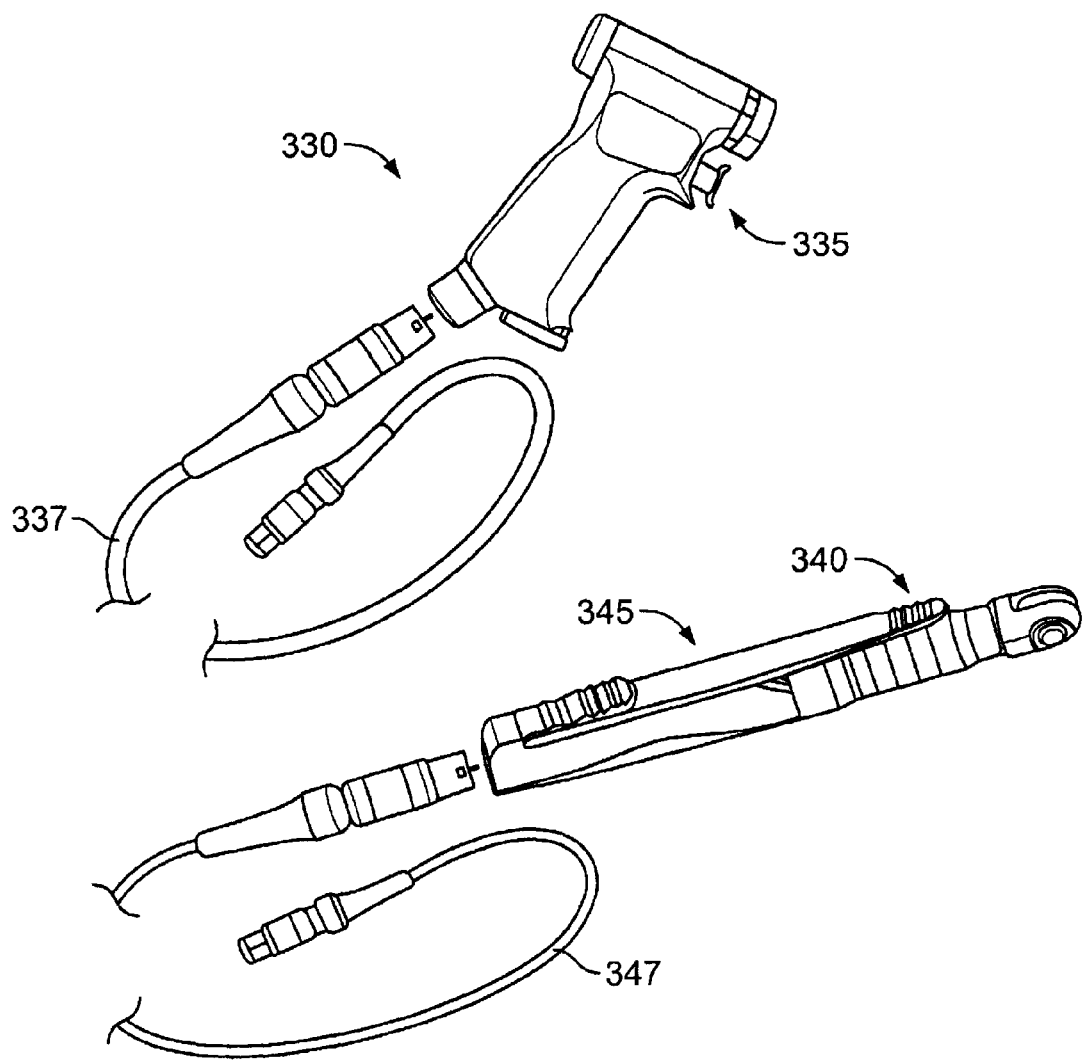
FIG. 3A is an illustration of perspective views of powered instruments.

Referring to FIG. 3A, powered instruments, such as drill 330 and saw 340 can also be used in conjunction with the console 110. The powered instruments 330 and 340 include triggers 335, 345, respectively, used to control operation of the powered instruments 330, 340. The powered instruments 330 and 340 can be connected to the instrument ports 112, 114 on the front panel 185 of the console via cables 337, 347, respectively. As discussed above, once connected to the instrument ports 112, 114, the console 110 can automatically detect the presence of the powered instruments 330, 340.

Figure 4A:
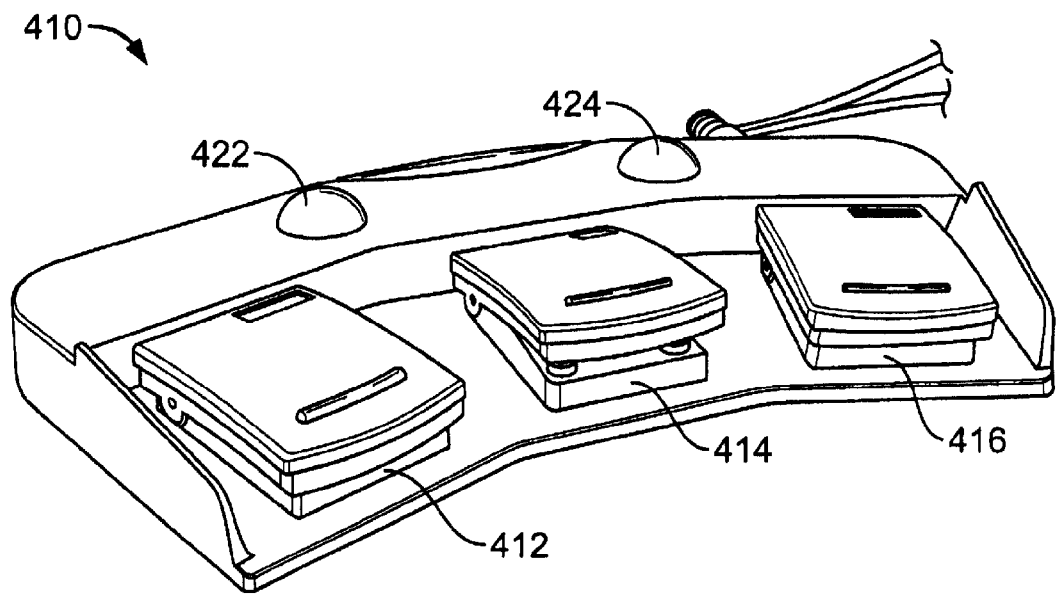
FIG. 4A is a perspective view of a footswitch of the system of FIG. 1.
Figure 4B:
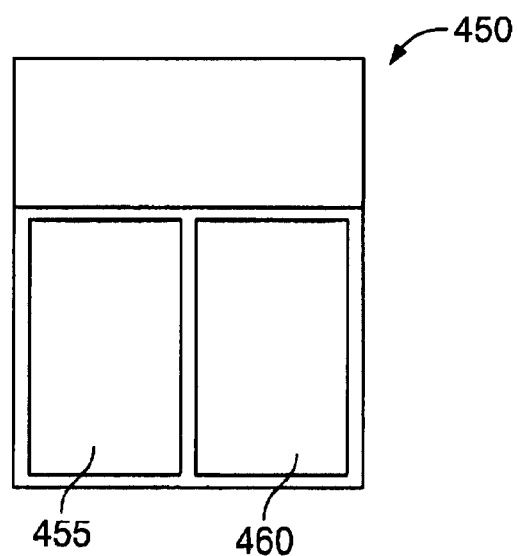
FIG. 4B is a schematic view of an alternative footswitch.

Referring to FIGS. 4A and 4B, footswitches 410 and 450 are shown. Either of the footswitches 410 and 450 can be used as the footswitches 140 and 140a. The footswitches 410 and 450 are connected to the port 116 of the console 110 through wired or wireless links. Wired communications take place via a RS-485 serial communication port or other wired links or connections, and wireless communications take place via a Bluetooth link and protocol or other wireless links or protocols. The footswitches 410, 450 communicate information about themselves and the position of their pedals to the console 110. The footswitches 410, 450 control forward, reverse, oscillate, and window lock modes of motor operation. The footswitches 410, 450 control one instrument at a time, and they can be configured to control either the instrument connected to the port 112 or the instrument connected to the port 114. As described in more detail below, the operation of the footswitches 410, 450 can be modified through an interface displayed on the screen 120 of the console 110. Two modes of operation are available, On/Off and Variable.

Referring to FIG. 4A, the footswitch 410 has three control pedals 412, 414, 416 and two switches 422 and 424. The pedal 412 is considered the "left pedal," the pedal 416 is considered the "right pedal," and the pedal 414 is considered the center pedal. The pedal 412 and the pedal 416 default to reverse and forward, respectively. Thus, depressing the pedal 412 or the pedal 416 causes the console 110 to supply power to an instrument connected to the console 110 (such as the surgical device 300) such that the inner member 315 of the blade 300 is driven in the selected direction. While the pedal 412 and the pedal 416 default to reverse and forward, respectively, the pedals 412, 416 can be configured to operate the surgical device 300 in the opposite direction. The center pedal 414 is configured to cause the surgical device 300 to oscillate. That is, depression of the center pedal 414 causes the console 110 to send position profile control signals to the surgical instrument 325, thus causing the inner member 315 to oscillate. The console 110 continues to send the control signals to the surgical instrument 325 until pedal 414 is no longer depressed.

When the footswitch is operating in variable or analog mode, the amount of depression of the pedal 412, 414, and 416 determine the percentage of set speed the instrument operates at; 100% of set speed is when the pedal is fully depressed and 0% of set speed (stop) is when the pedal is fully released. When the footswitch is operated in On/Off or digital mode, the pedals 412, 414, and 416 operate the instrument either at 100% of set speed or 0% of set speed (stop). In another implementation, maximum pressure establishes 100% of set speed with each new press of the pedals 412, 414, and 416, and decreasing pressure on the pedals 412, 414, and 416 allows deceleration of the instrument until the instrument stops. Pressing a footswitch pedal signals the console 110 to accelerate the instrument until the instrument reaches the set speed, and the set speed is maintained until the button is released. The pedals 412, 414, 416 on the footswitch 410 turn the motor drive on or off in a specific direction. Thus, the footswitch 410 allows the pedals 412, 414, and 416 to control speed as well as blade direction.

The footswitch 410 also includes two switches 422, 424. The switches 422 and 424 provide control for a Blade Window Lock function, described in more detail below, and a Lavage function, respectively, through a signal that travels from the footswitch 410 to the pump 150 through the bidirectional port 152.

Referring to FIG. 4B, the footswitch 450 includes two foot pedals 455 and 460 to control motor action. Each of the pedals 455 and 460 is referred to as the forward pedal or the reverse pedal depending upon configuration. The footswitch 450 includes contact switches (not shown) coupled to each pedal. The contact switches operate in the On/Off mode, such that each press of the pedal 455 or the pedal 460 starts or stops the instrument. Pressing the pedals 455, 460 simultaneously causes the console 110 to send signals to the instrument such that the instrument oscillates.

Figure 5:
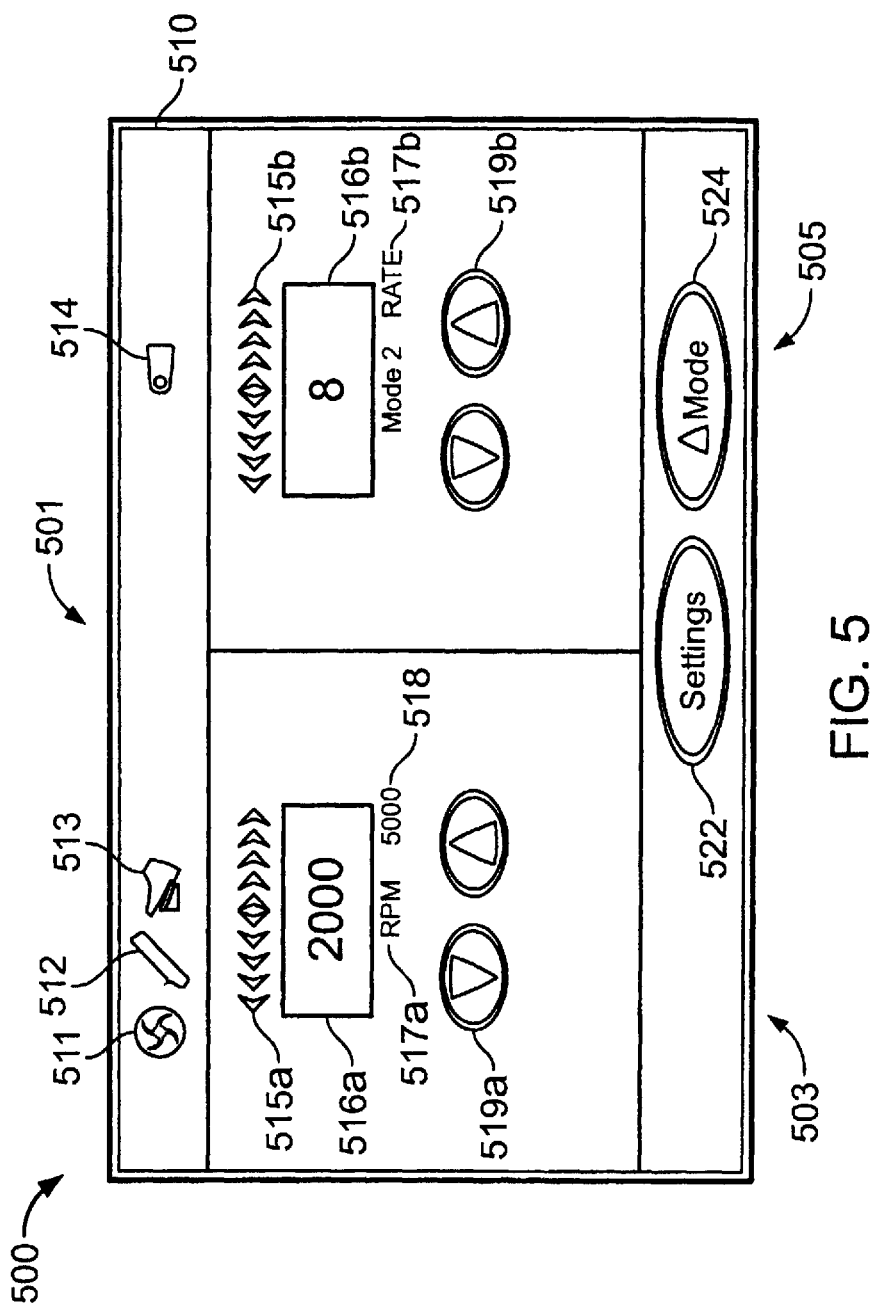
FIG. 5 is an illustration of a control screen of the console of FIG. 2A.

Referring to FIG. 5, an interface 500 shown on the display 120 of the console 110 provides a control screen 501 including graphical status indicators and touch screen control over the operation of motors associated with instruments connected to the console 110. The control screen 501 includes indicator and control sections 503 and 505, which are respectively associated with the instrument port 112 (also referred to as "Port A") and instrument port 114 (also referred to as "Port B"). The section 503 is on the left hand side of the control screen 501 and the section 505 is on the right hand side of the control screen 501.

As discussed above with respect to FIG. 2A, the system controller board 124 communicates control and parametric data bi-directionally with the motor controller board 123. Using a set of system interfaces, a controlling application provides the graphical status indicators and the touch screen control, thus allowing a user of the console 110 to have control over the instruments connected to the console 110 through the control screen 501 of FIG. 5. The system interfaces are hardware initialization and access functions to resources of the system controller board 124 that are used by the controlling application. The system interfaces include a bootstrap for Windows CE 4.2, peripheral Windows CE device drivers, a Windows CE USB driver, and a specialized Windows CE device driver, or other applicable system interfaces.

Figure 6:
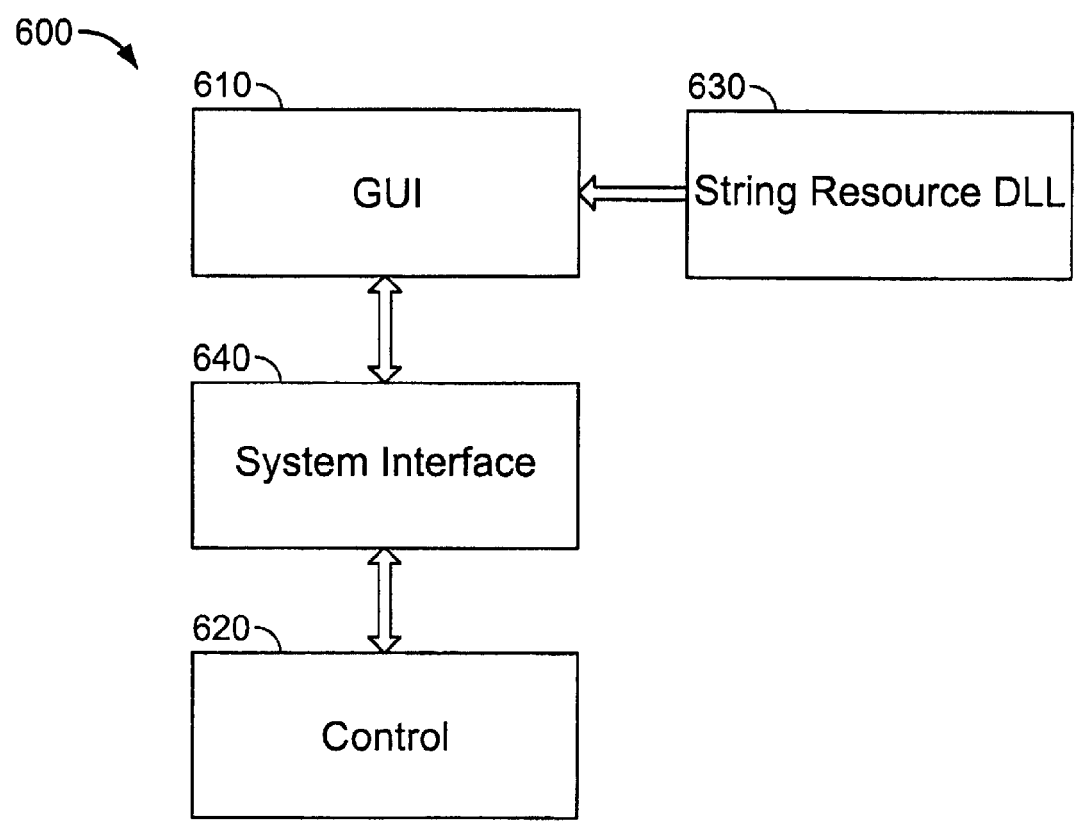
FIG. 6 is an illustration of an architecture of an application of the console of FIG. 2A.

FIG. 6 illustrates an architecture 600 of the controlling application used with the system controller board 124. The architecture 600 includes three modules, a graphical user interface module 610, a control module 620, a string resource module 630, and a system interface 640. The graphical user interface module 610 generates the graphical user interface (such as the control screen 501) and the displayed icons, accessories, and accessories controls. The control module 620 notifies the graphical user interface module of a change in state (such as the connection or removal of an instrument from the instrument port 112 or the instrument port 114). The string resource module 630 is a dynamically linked library (DLL) that supplies the graphical user interface module 610 correct strings depending on the selected language used to present commands in the control display 501. Each language that is supported by the console 110 has an associated DLL that is loaded when the console 110 is powered on or when the language setting is changed within the control display 501. Interactions between the controlling application and the motor controller board 123 are handled by the system interface 640.

The control module 620 continuously monitors the status of the instrument port 112 and the instrument port 114 to determine if an instrument is installed in either or both of the instrument ports 112 and 114. When an instrument is detected in the instrument port 112, the control module 620 notifies the graphical user interface module 610 and the graphical user interface module 610 displays data and accessories associated with the instrument in the section 503 of the control screen 501. If the instrument is removed from the instrument port 112, the control module 620 notifies the graphical user interface module 610, which in turn removes the data and accessories associated with the instrument from the section 503 of the control screen 501. Similarly, when an instrument is detected as connected to the instrument port 114, the control module 620 notifies the graphical user interface module 610 and the graphical user interface module 610 displays data and accessories associated with the instrument in the section 505 of the control screen 501. If the instrument is removed from the instrument port 114, the control module 620 notifies the graphical user interface module 610, and the data and accessories associated with the instrument are removed from the section 505 of the control screen 501.

In certain implementations, one or more of the instruments connected to the instrument ports 112, 114 include a motor drive unit (MDU). If a MDU is detected in either or both of the instrument ports 112 and 114, the control module 620 first determines whether the MDU is capable of hand control. If the MDU is not capable of hand control, a footswitch can be used to control the MDU. If the MDU is capable of hand control, the control module 620 monitors the status of the hand controls. The control module 620 also determines whether the connected MDU supports blade recognition, and if the MDU supports blade recognition, the control module 620 continuously monitors the blade type. The control module 620 notifies the graphical user interface module 610 that a MDU has been detected and the graphical user interface module 610 module displays the data and accessories associated with the MDU on the appropriate side of the control screen 501 (e.g., data and accessories associated with a MDU connected to the instrument port 112 are displayed in the section 503 and data and accessories associated with a MDU connected to the instrument port 114 are displayed in the section 505).

Figure 7:
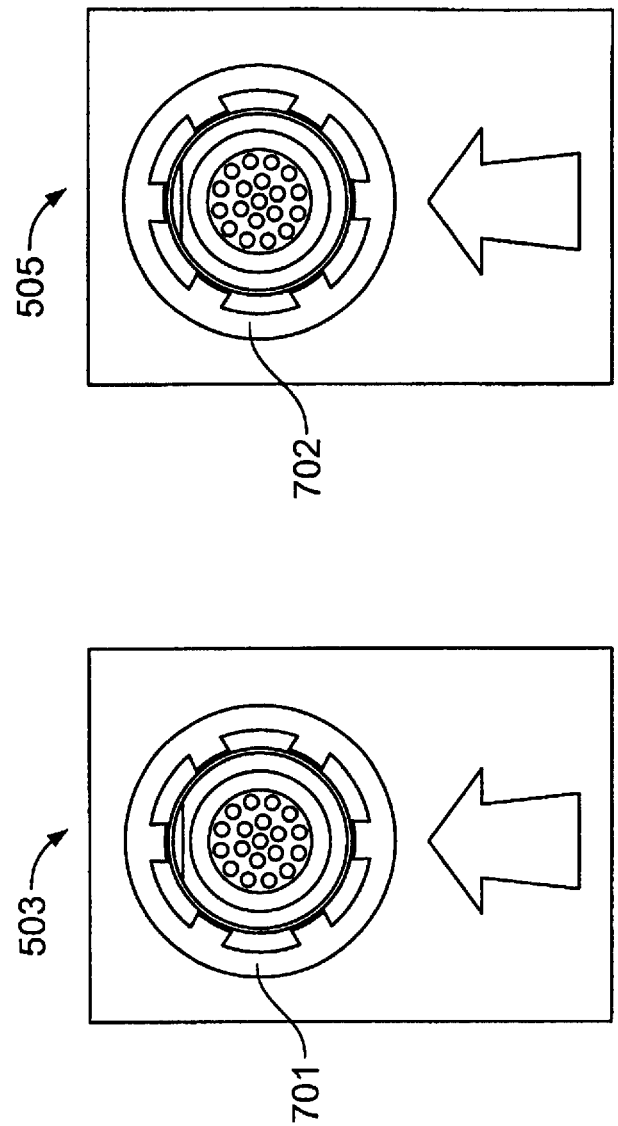
FIG. 7 is an illustration of a graphic included in a control screen of the console of FIG. 2A.

If the control module 620 detects instruments in both ports 112, 114, the data associated with both instruments is displayed in the control screen 501 in sections 503 and 505. The instruments in the ports 112 and 114 are operated independently, however, they can be operated simultaneously. Referring briefly to FIG. 7, if no instrument is detected in the instrument port 112, the section 503 of the control screen 501 displays the graphic 701, which indicates to the user that no instrument is connected to the port 112. Similarly, if the control module 620 does not detect the presence of an instrument in the port 114, the section 505 of the control screen 501 displays the graphic 702, which indicates to the user that no instrument is connected to the port 114.

Returning to FIG. 5, the control screen 501 includes an icon region 510, which displays icons 511, 512, 513, and 514 representing items connected to the console 110. The icons 511, 512, 513, and 514 are displayed upon notification from the control module 620 of the connection of an instrument, footswitch, or a connection to some other type of equipment to the console 110. The icons 511, 512, 513, and 514 also can have various display styles, with each display style representing a state of an instrument represented by the icon or the type of instrument connected. For example, the display style of icons 511, 512, 513, and 514 can be a particular color, shading, size, shape, and/or animation that represent a state or a type of instrument connected to the console 110. The icons 511, 512, 513, and 514 can also be implemented as bitmaps.

In the example shown in FIG. 5, the icon 511 is displayed in the section 503 and indicates that a fluid management system or pump 150 is connected to the console 110. A display style of the icon 511 can provide additional information about the pump 150. For example, if the connected fluid management system is a pump, such as the pump 150, the control module 620 notifies the graphical user interface module 610 of the state of the pump. If the pump 150 is running, the control screen 501 displays and animates a rotating blue icon. Otherwise, the control screen displays a stationary grey icon. If the graphical user interface module 610 receives an indication from the control module 620 that the pump 150 has been disconnected from the control module 110, the icon 511 disappears from the control screen 501. The icon 511 also can change format depending on the state of the fluid management system. The icon 511 representing the pump 150 can be in the section 503, which corresponds to "Port A," or the section 505, which corresponds to "Port B," depending on a mapping specified in a settings menu accessible through the control screen 501. Thus, the pump 150 can be set to be integrated with an instrument connected to either the instrument port 112 or the instrument port 114. When the pump 150 is integrated with the instrument connected to the instrument port 112, the pump 150 responds to commands from the instrument and footswitch connected to the instrument port 112. Similarly, if the pump 150 is integrated with the instrument port 114, the pump 150 responds to commands from the instrument and footswitch connected to the instrument port 114. In some implementations, the Lavage button 424 works only when the footswitch 410 and the pump 150 are connected to the same instrument port.

Additionally, upon notification of connection to a fluid management system, such as pump 150, an outgoing serial-communication packet is automatically updated by the control module 620 and/or the graphical user interface module 610. The outgoing serial-communication packet is transmitted to the connected pump 150 through the bi-directional port 152 during the initial connection and when a change in data occurs. A "Lavage Toggle" command is also transmitted in the event that a Lavage button is pressed on a connected footswitch that supports this functionality. The outgoing serial-communication packet typically includes a number of bytes in a data structure.

Referring back to FIG. 5, upon notification from the control module 620 of the insertion of an instrument, such as surgical device 300, motor drive unit (MDU) 325, or a powered instrument, such as a drill, saw, etc. into the instrument port 112 (e.g., "Port A") of the console 110, the graphical user interface module 610 displays the icons 512, 514 in the section 503, which correspond to the instrument ports 112, 114. If the graphical user interface module 610 receives a disconnect notification from the control module 620 indicating that the instrument has been disconnected from the instrument port 112, the icon 512 is removed from the icon region 510 or otherwise no longer displayed. Similarly, upon notification from the control module 620 of the insertion of a MDU into the instrument port 114 ("Port B"), the graphical user interface module 610 displays a yellow MDU icon (not shown) in the section 505, which corresponds to the instrument port 114. If the graphical user interface module 610 receives a disconnect notification from the control module 620, the MDU icon is removed.

Display of the icon 513 indicates that a footswitch has been connected to the console 110. The icon 513 is removed from the screen when the graphical user interface module 610 receives a disconnect notification indicating that the footswitch is no longer connected to the console 110. In the example shown in FIG. 5, the icon 513 is displayed in the section 503, which corresponds to the instrument port 112 (Port A). If a footswitch is connected to the console 110, the icon 513 is displayed in either the section 503 or the section 505 depending on a mapping selected in a settings menu.

Upon notification from the control module 620 of the insertion of an instrument, such as a sagittal saw, in the instrument port 114, the graphical user interface module 610 displays the icon 514 in the icon region 505. When the graphical user interface module 610 receives a disconnect notification from the control module 620 indicating that the saw has been disconnected from the instrument port 114, the icon 514 is removed from the screen. Similarly, when the control module 620 notifies the graphical user interface module 610 that a saw has been inserted into the instrument port 112, an icon (not shown) representing the saw is displayed in the section 503. The icon representing the presence of the saw in the instrument port 112 and the icon 514 representing the presence of the saw in the instrument port 114 can have different display styles while still providing a visual representation that the icons correspond to the same instrument. For example, the icon representing insertion in the instrument port 112 can be yellow and the icon 514 can be blue, but the icons can be the same shape and size.

Other types of icons can be displayed to indicate the presence of particular instruments, connections, or tools. For example, upon notification from the control module 620 of a digital control system connection, such as Smith & Nephew Inc.'s a CONDOR™ control system, the graphical user interface module 610 displays an icon (not shown) in the upper right hand corner of the control screen 501. If the graphical user interface module 610 receives a disconnect notification, the icon is removed from the control screen 501. Upon notification of a digital control system connection, an outgoing data packet is automatically updated by the control module 620 and/or the graphical user interface module 610 so that when a host requests a packet, the data is updated. When an incoming command from the host is found to be valid, the control module 620 and/or the graphical user interface module 610 is notified of the request and initiates the requested command.

The control screen 501 also includes direction indicators 515a and 515b, which indicate a direction or type of motion of the instruments connected to the instrument ports 112 and 114, respectively. In the example shown in FIG. 5, the direction indicators include both forward and reverse arrows that point in opposite directions in the center, which indicate that the instruments connected to the instrument ports 112 and 114 oscillate. The arrows in the direction indicators 515a and 515b point to the right when the respective instrument is set to forward motion, and the arrows in the direction indicators 515a and 515b point to the left when the respective instrument is set to reverse motion.

The control screen 501 also displays current speed settings 516a and 516b for the instruments connected to the instrument ports 112 and 114, respectively. The current speed settings 516a and 516b show speed and an associated unit of measure 517a and 517b (for example, rotations per minute as shown in FIG. 5). The current speed settings 516a and 516b also include an outline box that can be color coded, and the color can indicate which of the instrument ports 112 and 114 is associated with the current speed settings 516a and 516b.

The control screen 501 can include the maximum speed 518 for an instrument connected to the instrument port 112. If an instrument is connected to instrument port 114, the maximum speed for that instrument would be displayed on the section 505 of the control screen 501 in a similar manner. The decrement/increment controls 519a and 519b allow setting of the current speed of the current speed settings 516a and 516b, respectively. The current speed values can be adjusted within a range of numeric values, and the values are adjusted by pressing the decrement/increment controls 519a and 519b. The control module 620 receives a notification from the graphical user interface module 610 of a change in set speed, and the control module 620 changes the speed of an instrument connected to the indicated instrument port. When the set speed reaches the minimum or maximum speed for the instrument, the decrement/increment controls 519a and 519b disappear. The adjustment of the current set speed can occur automatically at a fixed repeat rate if the decrement/increment button 519a or 519b is held down for a second or more, and the automatic adjustment ceases when the adjustment button is released or when the current set speed reaches a minimum or maximum for the instrument.

The graphical user interface module 610 displays the data and accessories associated with the connected MDU on the appropriate side of the control screen 501. The data and accessories include the direction indicators 515a and 515b, the current speed settings 516a and 516b, the color-coded outline around the current speed settings 516a and 516b, the unit of measure 517a and 517b, the maximum range 518, and the decrement adjustment button and the increment adjustment button 519a and 519b. Default speed settings and maximum speed is particular to the connected instrument and is determined by specifications of the connected instrument, which can be stored in a table on the console 110 and accessed by the control module 620 and/or the graphical user interface module 610. For example, a MDU may have a range of forward motion speeds from 100 to 5000 rotations per minute, a default speed of 3000 rotations per minute, the same range of speeds and the same default speed for reverse motion, a speed range of 500 to 3000 rotations per minute in oscillate mode, and a default of 1000 rotations per minute in oscillate mode. If the MDU supports blade recognition, the default values and the ranges are determined taking into account the blade type.

When a MDU is detected, the current mode of operation is set to oscillate by default and the oscillate direction indicators are displayed in white on the appropriate direction indicator 515a and 515b depending on which instrument port into which the MDU was connected. Pressing a forward hand control button on the MDU causes the control module 620 to notify the graphical user interface module 610, and the forward direction indicators are displayed in the appropriate direction indicator 515a or 515b (e.g., all arrows point to the right in the appropriate direction indicator). Similarly, if a reverse hand control button is pressed on the MDU, reverse direction indicators are displayed on the appropriate direction indicator 515a or 515b (e.g., the direction indicator shows all arrows pointing to the left). If the forward hand control button on the MDU is held down for a second or more, the speed of the MDU alternates between two speeds while displaying the forward direction indicators in the appropriate direction indicator 515a or 515b. Releasing the forward button on the MDU results in the current speed setting being the most recent set speed value. Similarly, holding the reverse hand control button for a second or more results in the set speed alternating between two speeds while the reverse direction indicators are displayed in the appropriate direction indicator 515a or 515b.

If an oscillate hand control button is pressed on the MDU, the direction indicator 515a or 515b corresponding to the instrument port in which the MDU is connected displays oscillate direction indicators (e.g., left- and right-pointing arrows are shown with the arrowheads pointing in opposite directions in the center of the direction indicator). Additionally, if the oscillate hand control button on the MDU is pressed and held down for about a second or more, the control module 620 will notify the graphical user interface module 610 and the direction indicator 515a or 515b shows the window-lock direction indicators (e.g., left- and right-pointing arrows are shown with arrowheads coming together in the center of the direction indicator).

Additionally, when a MDU is detected, the control screen 501 can display the maximum rotations per minute (RPM) or other unit of measure, depending upon the current MDU mode of operation, in the appropriate unit of measure display 517a and 517b. If the current mode of operation of the MDU is forward, reverse, or Oscillate Mode 1, the unit of measure is RPM and the maximum RPM for the MDU is displayed in 518. If the current mode of operation of the MDU is Oscillate Mode 2, the unit of measure is rate rather than RPM. Oscillate Mode 1 is a velocity-controlled method of ramping motor speed from zero to a specified target speed and then ramping the motor speed from the target speed to zero again in a specified period of time. Oscillate Mode 2 is a position-controlled method of ramping motor speed in which the motor accelerates and decelerates to a specified position in a specified period of time and then reverses direction and returns to the starting position. Oscillate Mode 1 is available for all MDUs, but neither mode is typically available for powered instruments such as drills and saws, which run unidirectionally.

If the control module 620 determines that the MDU is in a running state, the graphical user interface module 610 is notified by the control module 620 and the control display 501 is updated to reflect the running state. For example, the color of the arrows in the direction indicators 515a and 515b can be colored green and the background color of the appropriate current speed setting 516a or 516b can change. If the MDU is turned off, the background color of the appropriate current speed setting 516a or 516b changes to reflect the new state of the MDU.

If a powered instrument is connected to the console 110, the control module 620 monitors the status of the hand controls on the powered instrument to determine if the powered instrument supports direction control. The powered instrument can be, for example drill 330 or saw 340 (FIG. 3A). A drill may support forward and/or reverse operation, and a saw supports a mechanical oscillate mode of operation. The control module 620 notifies the graphical user interface module 610 that a powered instrument has been detected in the connection port 112 and/or 114, and the graphical user interface module 610 displays the data and accessories associated with the powered instrument on the appropriate side of the control screen 510 (e.g., in section 503 or 505).

For powered instruments, sections 503 and 505 include direction indicators 515a and 515b, and the direction indicators 515a and 515b display a percentage of full speed associated with the current set speed, a color coded outline around the current set speed, and the decrement/increment controls 519a and 519b. The percentage of full speed is adjusted by pressing the decrement/increment controls 519a or 519b, and the decrement/increment controls 519a and 519b disappear when set speed reaches the maximum or minimum for the powered instrument. The default speed range is 10%-100% in ten-percent increments, and the default setting is 50% of full speed for the drill and 100% of full speed for the saw. The percentage of full speed is adjusted automatically at a fixed percentage amount if either the increment or decrement button is held down. The adjustments cease when the decrement/increment control 519a or 519b is released or when the percentage of full speed has reached its minimum or maximum.

A trigger located on the powered instrument can be used to activate it. The amount of depression of the trigger determines the actual speed of the powered instrument, and the trigger can be used to vary the speed of it. When the trigger is released, the powered instrument is stopped, and fully depressing the trigger results in the speed of the powered instrument being a percentage of full speed of the powered instrument as shown in a current set speed indicator 516a or 516b. If a footswitch is used, trigger operation of the powered instrument is suspended until the footswitch releases control, and trigger operation of the powered instrument blocks the footswitch until the trigger releases control. When a powered instrument is connected to the instrument port 112 or 114, the controlling application ignores the Window Lock and Lavage footswitch button functions. Adaptive trigger calibration captures the maximum and minimum analog values measured during use of the powered instrument and expands an active trigger ON region accordingly. To prevent locking in an out-of-range value, if a powered instrument is connected to the console 110 with the trigger depressed, the ON limit (TriggerMin) is reset with the OFF limit (TriggerMax) leaving an initial ON region of 15 ADC counts. The ON region is allowed to re-expand during normal trigger operation. A small hysteresis band (e.g., 15 ADC counts), applied to the decision to recalibrate OFF limit (TriggerMax) and reset the ON limit (TriggerMin), minimizes unnecessary recalibrations.

A deadband bounding the trigger ON region at both limits serves a dual purpose. On the TriggerMax side, it accommodates the voltage change incurred by lever trigger units from the sliding magnet trigger lock mechanism. Here, this band is required to allow the release of the trigger lock, causing a corresponding drop in trigger voltage, without inadvertent motor actuation. On the TriggerMin side, it prevents motor velocity changes at the maximum trigger position caused by mechanical slop in the trigger assembly.

Additionally, if the console 110 detects a problem or failure, the console 110 displays a warning (not shown) on the control screen 501. For example, the warning can be a yellow box located near the bottom of the control screen 501. Touching the displayed warning opens a full description of the error or failure that caused the warning. A button (such as an "OK" button) can be pressed to close the warning message and return to the control screen 501. When the console 110 encounters a system fault, the console 110 stops operation of the attached instruments, sounds an alarm, clears the control screen 501, and displays a fault message.

The control display 501 also includes a change mode control or settings button 522, selection of which allows a user to specify preferences for oscillation modes, footswitches, pump interface, language, etc. If a MDU is not active, connected to the connection port 112 or 114, supports two oscillation modes and was last active in oscillate mode or was just connected, the change mode control 524 is displayed. Selection of the change mode control 524 will toggle the MDU between oscillate modes as provided in more detail below. The control display 501 also includes a settings control 522, selection of which produces a settings menu through which a user can configure various settings of the console 110 once all of the instruments and other devices have been connected to the console 110. The settings control 522 is active whenever the MDUs and powered instruments connected to the console 110 are not running.

Figure 8:
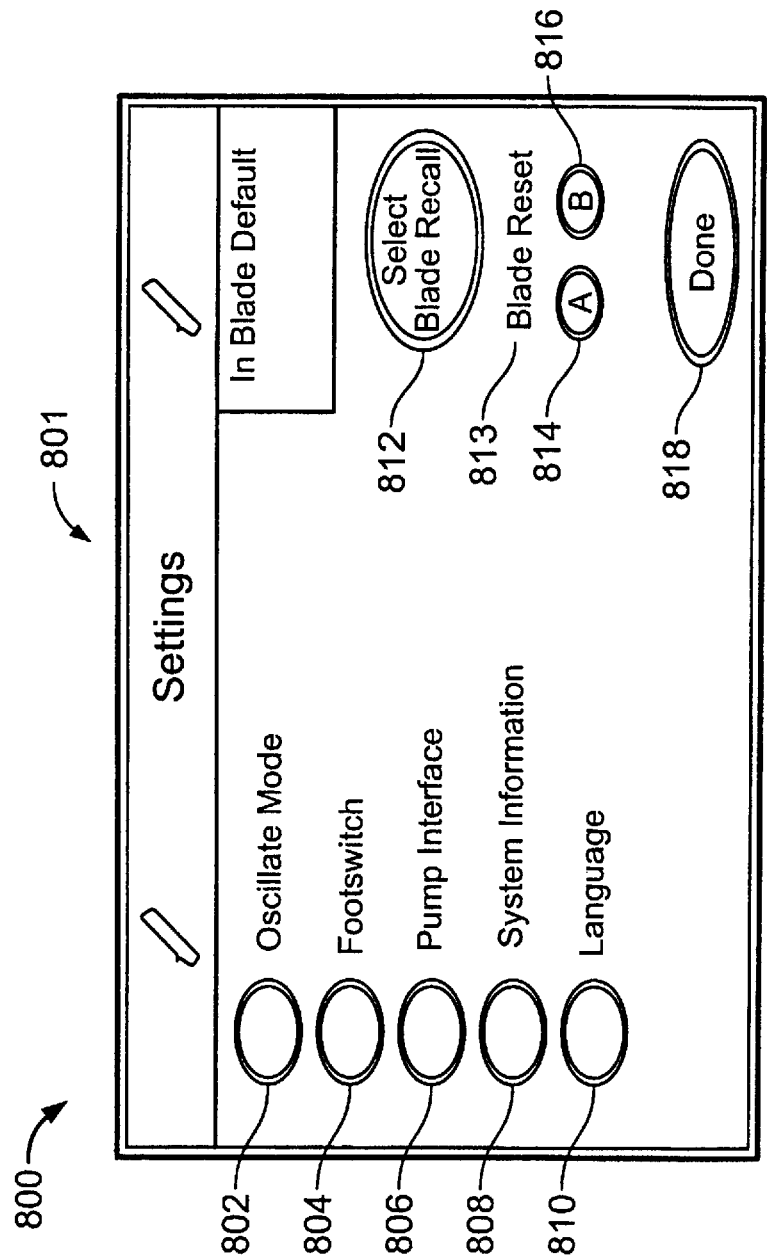
FIG. 8 is an illustration of a settings screen of the console of FIG. 2A.

Referring to FIG. 8, an interface 800 shown on the display 120 shows a settings screen 801 that allows users to specify preferences and parameters for the operation of peripherals connected to console 110. The settings screen 801 is displayed in response to a selection of the settings control 522 (FIG. 5). The settings screen 801 includes an oscillate mode control 802, a footswitch control 804, a pump interface control 806, a systems information control 808, and a language control 810. The settings screen 801 also includes a blade mode control 812, blade reset text 813, blade reset controls 814 and 816, and a completion or "Done" control 818.

The oscillate mode control 802 allows the user to program oscillate mode settings. The console 110 supports two oscillation modes and these two modes may be referred to as Oscillate Mode 1 and Oscillate Mode 2. Oscillate Mode 1 is a velocity-controlled method of ramping motor speed from zero to a specified target speed and then ramping the motor speed from the target speed to zero again in a specified period of time. Oscillate Mode 2 is a position-controlled method of ramping motor speed in which the motor accelerates and decelerates to move a motor shaft to specified positions in specified periods of time to enable reversal of direction to return to the starting position. Oscillation can be based on a desired time period (Mode 1) or a set number of revolutions (Mode 2). Oscillate Mode 1 is the default oscillation mode.

Referring to FIG. 9A, selection of the oscillate mode control 802 opens an oscillate mode screen 910, which allows adjustment to the oscillation profile of the instrument connected to either the instrument port 112 ("Port A") or the instrument port 114 ("Port B"). The screen that opens depends upon the last oscillate mode used for the instrument port selected. A control 912 allows the user to customize the oscillate mode activated for the instrument connected to the instrument port 112 (e.g., "Port A"), and a control 914 allows the user to customize the oscillate mode activated for the instrument connected to the instrument port 114 (e.g., "Port B"). If the surgical instrument attached to the selected port will operate in either Oscillate Mode 1 or Oscillate Mode 2, pressing Adjust opens either the Mode 1 or Mode 2 screen, depending on which was last used for that port. Selection of a done control 916 returns the user to the previous screen, the settings screen 801.

Selection of the Port A control 912 or the Port B control 914 from the oscillate mode screen 910 launches oscillate mode onescreen 920 (FIG. 9B) if Oscillate Mode 1 was last used for that port. As noted above, Oscillate Mode 1 is based on a time interval. A time adjustment control 925 allows a user to set the number of seconds (e.g., the time interval) an instrument takes to make one forward or reverse period of oscillation as displayed in display 924. For example, the time may be adjusted in increments of 0.1 seconds by selecting the time adjustment control 925. When the time has reached the minimum or maximum of the instrument's oscillation range, the time adjustment control 925 disappears. In the example shown in FIG. 9B, the range of oscillation is 0.30 to 1.0 seconds for an oscillation period. Selection of the default control 926 restores the time to a default value. Selection of a cancel control 927 returns the user to the oscillate mode screen 910, without changing the current settings, and selection of a set control 928 notifies the control module 620 to save the current settings and to use the newly selected value before returning the user to oscillate mode screen 910.

Selection of the Port A control 921 or the Port B control 914 from the oscillate mode screen 910 launches Oscillate Mode 2 screen 930 (FIG. 9C) if Oscillate Mode 2 was last used for that port. As discussed above, Oscillate Mode 2 is based on a number of revolutions a blade completes before reversing directions. For example, the Oscillate Mode 2 can be set such that the blade completes 1 or 2 revolutions before reversing directions. The Oscillate Mode 2 screen 930 includes an adjustment control 935 to set a number of revolutions to rotate in each direction before reversal during oscillation. The number of revolutions is adjusted in increments of 1 revolution by pressing the adjustment control 935 and is displayed in display 934. The range of the adjustment is one to two revolutions. When the number of revolutions has reached the minimum or maximum of the range of possible revolutions for the instrument, the adjustment control 935 disappears. The default number of revolutions is restored by selecting the control 936. Selection of a cancel control 937 returns the user to the oscillate mode screen 910, without changing the current settings, and selection of a set control 938 notifies the control module 620 to save the current settings and to use the newly selected value before returning the user to oscillate mode screen 910.

Figure 10:
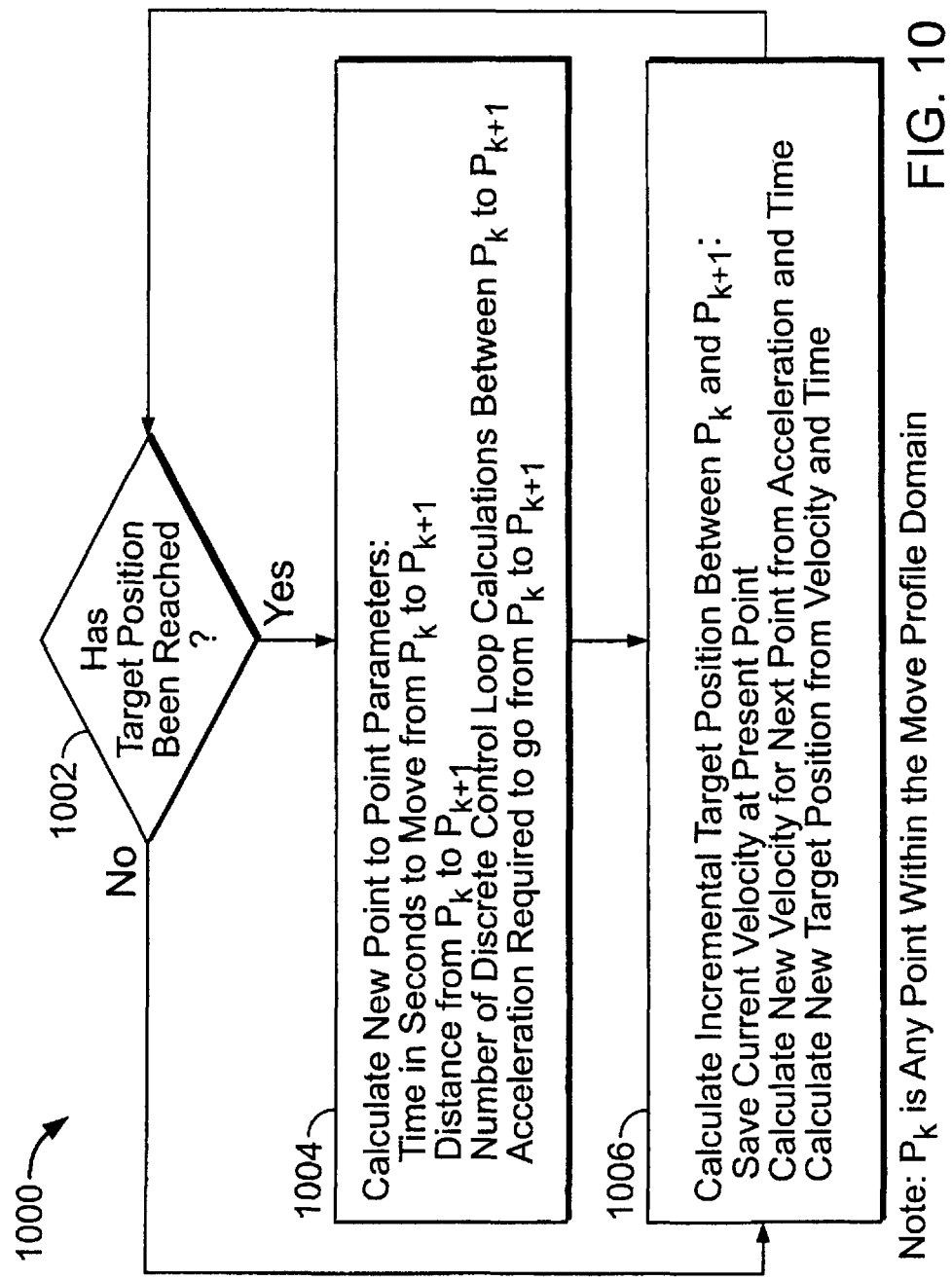
FIG. 10 is example process 1000 for moving a blade of an instrument.

Referring to FIG. 10, an example process 1000 for moving a blade of an instrument operating in Oscillate Mode 2 to a new position is shown. Blade Window Lock is used to set the stop position of the inner rotating blade (e.g., inner member 305 of FIG. 3) relative to the opening 320 of the outer member 310, as described in U.S. Pat. No. 5,602,449, which is incorporated by reference herein in its entirety. Window Lock is used in the position control methodology discussed herein to determine the initial position of the position profile ($P_i$). A position of a motor output shaft is determined from the motor's three armature position Hall Effect sensors and a gearhead ratio. Target motor shaft positions are calculated from a position profile that is defined by an array of coordinates in the form: percentage of time elapsed, and position, with position being defined in revolutions of output shaft. The period of time (in seconds) to transact one complete move profile is stored in the console 110. The position profile can be stored in a data structure that includes the percentage time coordinate, the revolution distance coordinate (which can specify distance as a number of revolutions), and a count variable that includes a number of point pairs defining the profile. Profiles that repeat end in the position from which the profile began to prevent creep (unless that is the intent).

To move the blade of an instrument operating in Oscillate Mode 2, it is determined whether a target position has been reached (1002). The target position can be a position specified in a coordinate of the position profile. If the target position has been reached, parameters to move to the next point in the profile are determined (1004). In particular, the time in seconds to move from the current position ($P_k$) to the next position ($P_{k+1}$), the distance from the current position ($P_k$) to the next position ($P_{k+1}$), and an acceleration to move from the current position to the next position are determined. Again, the current position ($P_k$) can be any arbitrary position within the move position profile. If the target position has not been reached, an incremental target distance between the current position and the next position is determined (1006). The current velocity is saved, a new velocity is calculated for the next point from acceleration and time, and a new target position is calculated from velocity and time. Table 1 shows an example position profile.

TABLE 1

| Point | % time | distance (number of revolutions) |
|---|---|---|
| $P_i$ | 0 | 0 |
| $P_{i+1}$ | 5 | 1 |
| $P_{i+2}$ | 10 | 2 |
| $P_{i+3}$ | 50 | 2 |
| $P_{i+4}$ | 55 | 1 |
| $P_{i+5}$ | 60 | 0 |
| $P_{i+6}$ | 100 | 0 |

In the example shown in Table 1, $P_i$ is the initial position, and each point corresponds, in this example, to the window open position. For a complete move profile of 0.50 seconds, the first and second forward revolutions each occur in 0.025 seconds (5% time for each revolution), followed by a hold period with the window open of 0.2 seconds (40% time), followed by two reverse revolutions each in 0.025 seconds (5% time for each revolution), followed by a hold period with the window open of 0.2 seconds (40% time). The cycle is then repeated. The hold periods act to reduce clogging of the blade and enhance resection by evacuating material out of the blade and then pulling more material into the blade to be cut in the next cycle.

The number of revolutions prior to direction reversal can be other than two revolutions, for example, one or three revolutions. The hold period can be other than 40% of the time for the complete move profile, for example, in the range of 10% to 40%. The optimum hold period is a function of the suction rate and the length of the blade. Furthermore, different profiles can be employed for different tissue types and/or for different blades. Table 2 shows an example of a simple triangular oscillate profile (Mode 2). In the example shown in Table 2, point of direction reversal occurs at $P_{i+2}$, since the distance (number of revolutions) begins to decrease beyond that point.

TABLE 2

| Point | % time | distance (number of revolutions) |
|---|---|---|
| $P_i$ | 0 | 0 |
| $P_{i+1}$ | 25 | 1 |
| $P_{i+2}$ | 50 | 2 |
| $P_{i+3}$ | 75 | 1 |
| $P_{i+4}$ | 100 | 0 |

Position control provides for high speed, complex blade motions. Referring to FIGS. 11A-11E, examples of various shaft position (S) vs. percentage of time (T) profiles are shown. Each of the profiles has unique and beneficial cutting attributes when matched with different tissue types and blade styles. The initial position for rotary or reciprocating blades can be set using window lock. The attributes listed below are non-limiting examples for a window lock position of open. FIG. 11A shows an oscillation profile with two forward and two reverse rotations per cycle and a 0.1 second period. Such a profile provides increased soft tissue resection rates. FIG. 11B shows a profile that is similar to the profile of FIG. 11A with the addition of a mini-oscillation cycle at the window open position at the end of the forward portion of the cycle. Profiles such as the profile shown in FIG. 11B are suited for biting off harder fibrous tissues such as an ACL stump. FIG. 11C shows a profile that corresponds to the hold profile discussed above. A profile such as the profile of FIG. 11C is suitable for reducing soft tissue clogging in toothless style blades. FIG. 11D shows a profile that is particularly adapted for a reciprocating style blade. The profile shown in FIG. 11D has an initial slow distal motion and speeds up near the distal-most portion of the stroke to cut tissue. The profile of FIG. 11D is suitable for cutting, for example, the meniscus. FIG. 11E shows a profile that illustrates the aperiodic motion capability of the position control methodology. Although not illustrated, profiles containing negative positions are fully supported.

Figure 12A:
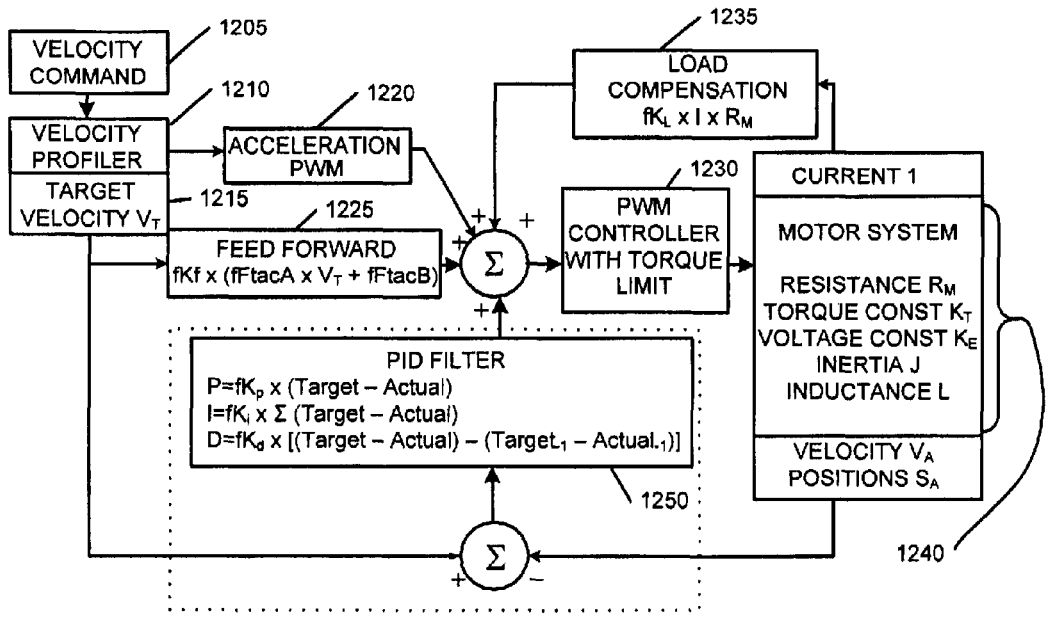
FIG. 12A illustrates a velocity control technique for controlling electrical power to a motor.

Referring to FIG. 12A, the target shaft position and actual shaft position become the inputs to a discrete time proportional-integral-derivative controller (PID) velocity control algorithm that controls the electrical power necessary to keep the motor shaft position on target and cause the motor to move at a particular velocity. Gain variables are used to scale values included in control blocks, and the values included in control blocks are summed and piped through filters to produce an output to the motor. Setting appropriate coefficients to zero allows the same variable structure and PID function to be used for both position and velocity control, as well as for different types of motors. A velocity command 1205 can include a target velocity set by a user of the console 110. The target velocity can be set in the user interface discussed above.

The velocity profiler 1210 determines increments and decrements of velocity of the motor over discrete time periods, and a target velocity 1215 is a velocity determined to move the motor to a target position at a particular velocity. An acceleration PWM module 1220 adds inertial compensation to the velocity. In particular, the acceleration PWM module adds a boost to accelerate a high-inertial load. A feed forward module 1225 is an open-loop estimate of how fast the motor would run without a load. The feed forward module 1225 applies voltage to the motor and translates voltage applied to the motor to the speed of the motor. The PWM controller 1230 acts as a torque limit and limits torque on the motor to a predefined threshold. A load compensation module 1235 indicates load on the motor in current and compensates for the load on the motor. The output module 1240 includes the resistance in the motor, torque and voltage constants, inertia of the motor, and inductance of the motor. The output module 1240 also indicates measurable parameters of the motor, including the velocity, current in the motor, and position of the motor. The actual velocity of the motor and the target velocity of the motor are input into a PID filter block 1250, and P, I, and D coefficients are determined in the filter block 1250.

Figure 12B:
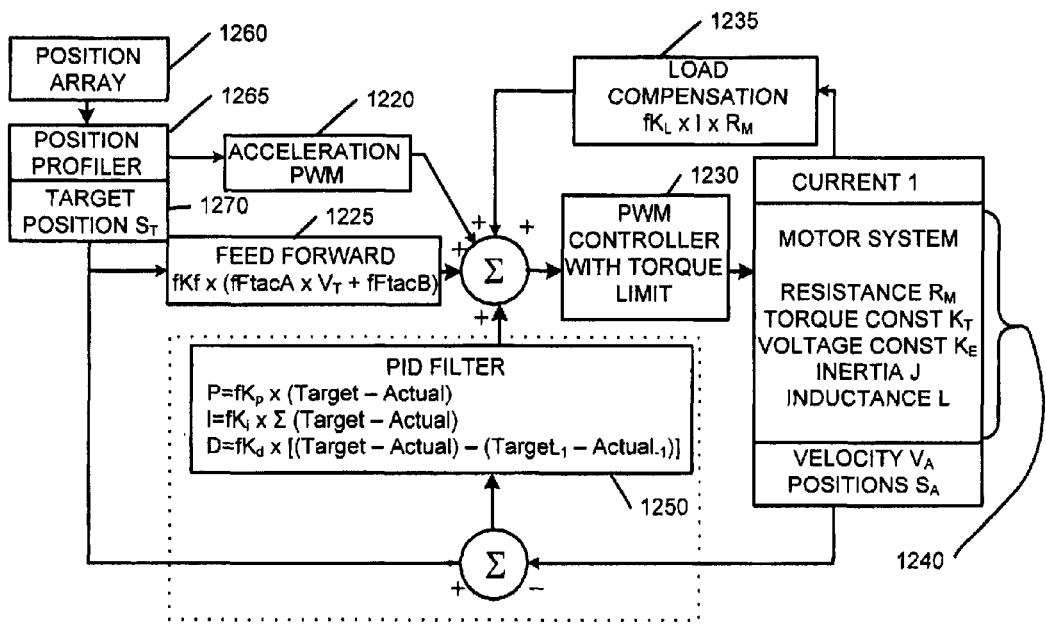
FIG. 12B illustrates a position control technique for controlling electrical power to a motor.
Figure 13:
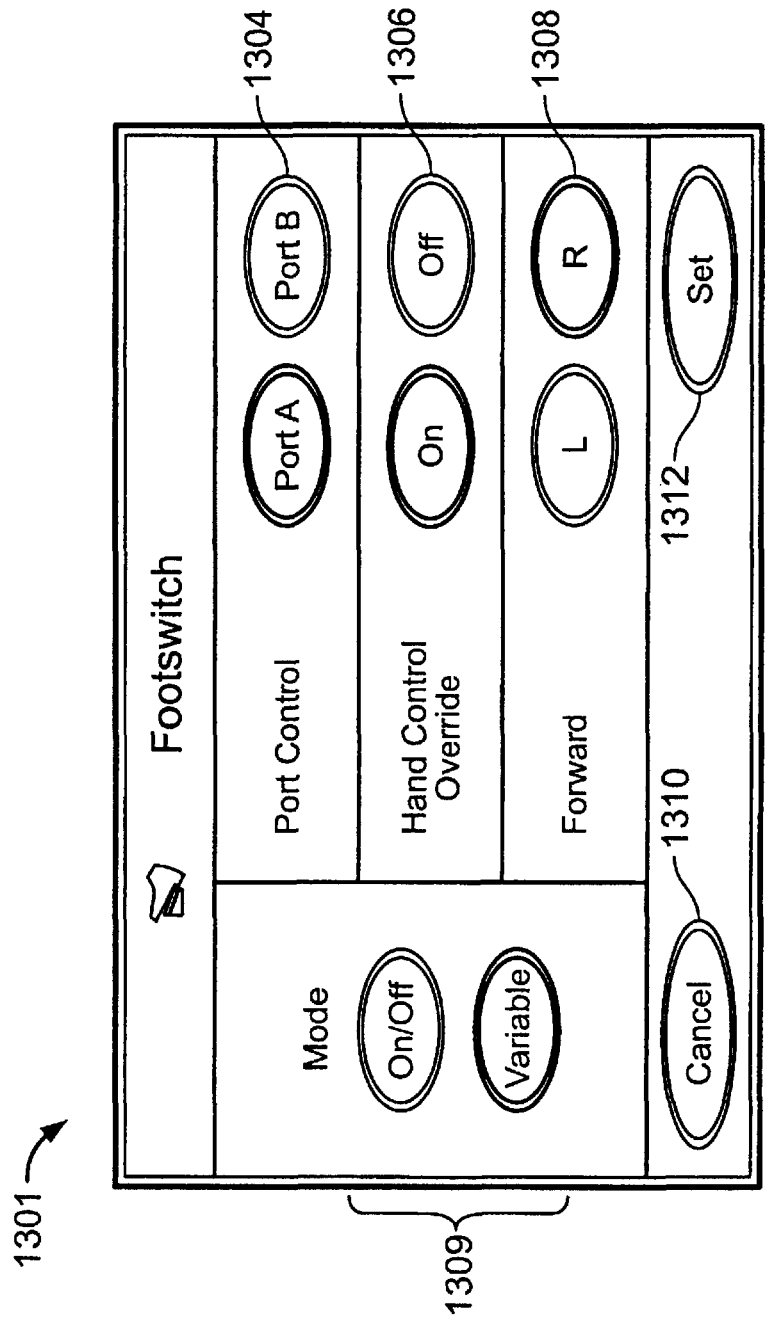
FIG. 13 illustrates a settings screen of the console of FIG. 2A.

Referring to FIG. 12B, a PID position control algorithm works similarly to the PID velocity control algorithm discussed with respect to FIG. 12A. In the position control algorithm, the coefficients of the feed forward module 1225 are set to zero. Instead of receiving a velocity command, an array of positions 1260 is provided to a position profiler 1265. The array of positions is positions in a position profile of the instrument (such as the profiles shown in FIGS. 11A-11E). A target position 1270 is compared to an actual position at the PID filter block 1250.

In addition to rotating blades, the position control methodology can also be applied to an axial, reciprocating blade. Here again, the movement of the blade can be controlled such that there is a hold period when the reciprocating blade is in its distal position with the window open. The position control methodology can also be used to slow down or stop a rotating blade in a predetermined window position when the blade is running in forward or reverse mode.

The position control methodology provides system precision and flexibility. Rather than using knowledge of shaft position to signal (trigger) a control algorithm when to stop or reverse (a velocity control algorithm), knowledge of shaft position is the input to the position control algorithm. Therefore, the stop position or point of shaft reversal is known in advance by the control algorithm as it computes the acceleration needed to move between the points of the position profile. The velocity control algorithm regulates the speed in which the shaft rotates asynchronously to its position. In a velocity control algorithm, the independent variables (inputs to, and controlled by, the control algorithm) are time, acceleration, and velocity, with the dependent variable (consequence of the control algorithm) being position. In the position control algorithm, the independent variables (inputs to, and controlled by, the control algorithm) are time and position, with the dependent variables (consequences of control algorithm) being velocity and acceleration.

Referring again to FIG. 8, the footswitch control 804 allows the user to configure the footswitch. Selecting the footswitch control 804 button from the settings screen will launch the footswitch screen 1301 shown in FIG. 13. The footswitch screen 1301 permits the user to configure the way the footswitch works. The graphical user interface module 610 is notified by the control module 620 of a selection of a port control 1304, a hand control override 1306, or a footswitch mode control 1308. Selection of a cancel control 1310 returns to the settings screen 801 without changing the current setting. Selection of the set control 1312 notifies the control module 620 to save the current settings and to use the newly selected settings before returning to the setting screen 801. The footswitch screen 1301 includes the port control 1304, which provides controls for assigning the footswitch to either instrument port 112 (e.g., Port A) or instrument port 114 (e.g., Port B). The currently selected port is indicated by shading in the example shown in FIG. 13. The footswitch drives the instrument connected to the selected port.

The footswitch screen 1301 also includes a hand control override 1306, which allows a hand control override feature of an instrument to be enabled or disabled. The hand control override 1306 allows the user to set the primary controls for controlling the motor of a connected MDU, and the current override setting is shown by shading. When the hand control override control 1306 is set to On, only the footswitch operates the instrument, and hand controls for that instrument do not operate. When the hand control override control 1306 is set to Off, either the hand controls or the footswitch can be used to operate the instrument. However, only one source of control can be used at one time (e.g., at a particular time, either the footswitch or the hand controls can operate the instrument).

The footswitch screen 1301 also includes the footswitch mode control 1308, which allows the user to change the forward and reverse pedal assignments on the footswitch. However, if the console 110 detects that the footswitch does not support re-mapping of the forward and reverse pedals, the user is not allowed to change the forward and reverse pedal assignments. For footswitches that support re-mapping of the forward and reverse pedals, selection of the "L" button will map the forward mode of operation to the left foot pedal of the footswitch. Selection of the "R" button will map the forward mode of operation to the right foot pedal of the footswitch.

The footswitch screen 1301 also includes a mode selection control 1309. The mode selection control 1309 allows the user to select to use the footswitch in an On/Off mode (which can be the digital footswitch mode discussed above) or a variable mode (which can be the analog footswitch mode discussed above). Briefly, in On/Off mode, depressing a footswitch pedal causes a instrument connected to the console 110 and controlled by the footswitch to operate at full set speed, and releasing the footswitch pedal turns the instrument off. Pressing a pedal of a footswitch that is operating in Variable mode causes the instrument speed to be adjusted based on pedal pressure. If the console 110 detects a footswitch that does not support variable mode operation, such as a Low Profile (On/Off) or Pedal-Style footswitch, the mode selection control 1309 does not appear on the footswitch screen 1301, and the footswitch operates in the On/Off mode. In the example shown in FIG. 13, the footswitch supports variable mode operation, thus the mode selection control 1309 is displayed, and the mode selection control 1309 can be used to select to operate the footswitch in either the On/Off or Variable mode. In the example shown, the user has selected to operate the footswitch in variable mode, and a button corresponding to the variable footswitch mode is shaded to indicate that variable mode is the active footswitch mode.

The footswitch screen 1301 also includes a cancel control 1310 and a set control 1312. Selection of the cancel control 1310 returns the user to the settings screen 801 without changing the current setting. Selection of the set control 1312 saves the current footswitch settings and returns the user to the settings screen 801.

Figure 14:
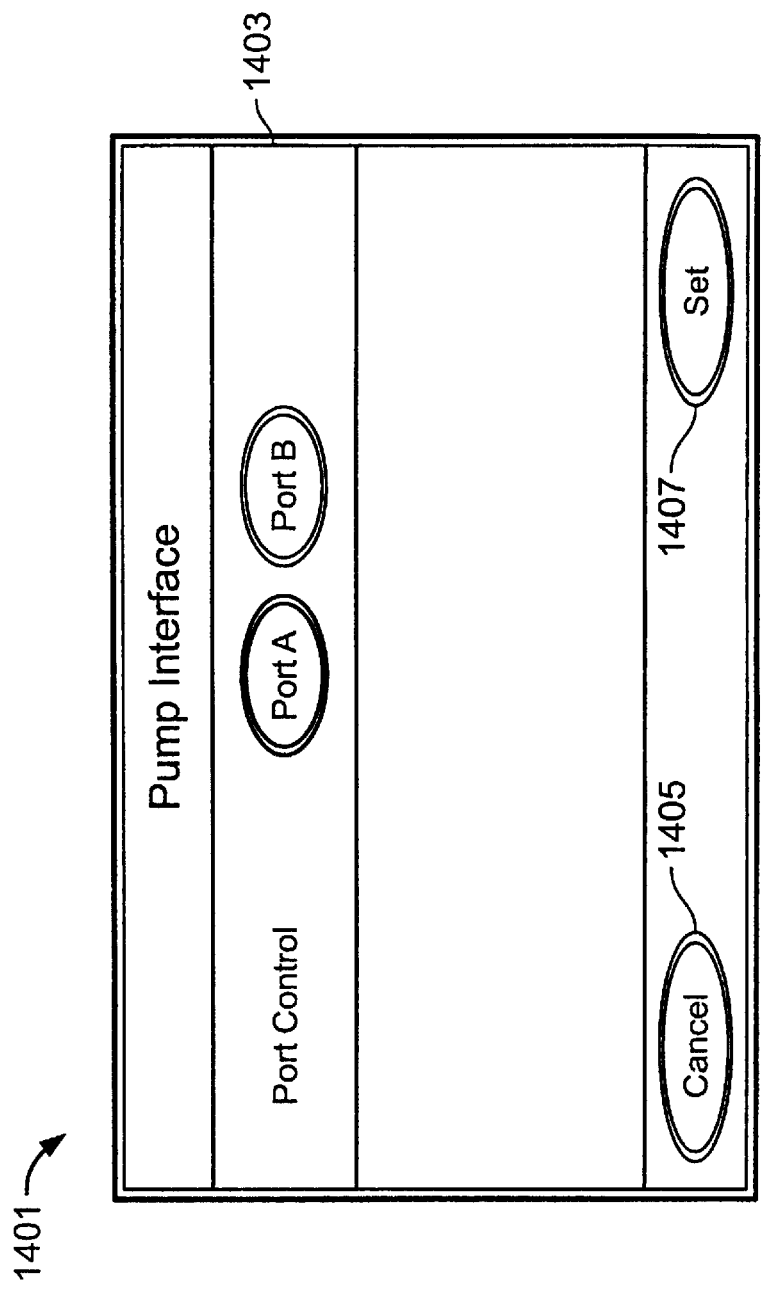
FIG. 14 illustrates a settings screen of the console of FIG. 2A.

Referring again to FIG. 8, selection of the pump interface control 806 causes a pump interface screen 1401 (FIG. 14) to appear. The pump or fluid management system operates from the MDU connected to the port to which the pump is assigned. For example, and referring to FIG. 14, for the pump to work with a MDU connected to the instrument port 112 ("Port A"), "Port A" is selected in a port control box 1403. The selected port is shaded to indicate selection of the port. In the example shown, Port A is selected, thus the pump works with an instrument connected to instrument port 112. Selection of the "Port B" button in the port control box 1403 results in the pump being assigned to work with the instrument connected to the instrument port 114 ("Port B") of the console 110. The pump interface screen 1401 also includes a cancel control 1405, selection of which returns the user to the settings screen 801 without changing the current settings. The set control 1407 saves the current settings shown in the pump interface screen 1401 and returns the user to the settings screen 801.

Selection of the system information control 808 of FIG. 8 causes a display of general information associated with the console 110, such as the product name, product reference number, software versions, application versions, and motor controller version. The language control 810 allows the user to specify the language in which commands and information are displayed. For example, selection of the language control 810 allows the user to select from among various languages such as English, German, French, and Italian.

The blade mode control 812 allows the user to select between using the console 110 in Blade Recall Mode or Blade Default Mode. When in Blade Recall Mode, the console 110 can be programmed with custom settings for blade forward speed, reverse speed, oscillate speed (oscillate mode 1) and oscillate rate (oscillate mode 2). If any settings are changed in Blade Recall Mode, the settings are saved until the settings are reset in Blade Recall Mode or the system is restored to default settings. When operating in Blade Default Mode, changes to blade settings are saved until the console 110 is powered down or the system is reset to Blade Recall Mode. The blade reset text 813 and blade reset controls 814 and 816 are displayed in the settings screen 801 when an instrument is in the instrument port 112 or the instrument port 114, respectively. Selection of the done control 818 returns the user to the control screen 501.

A number of implementations of the console 110 and surgical system 100 have been described. Nevertheless, it will be understood that various modifications may be made without departing from the spirit and scope of the application. For example, while the console 110 has been described with respect to control of surgical instruments, the console 110 could be used with handheld instruments in non-surgical settings, and the console 110 and associated control systems could be used with various types of instruments, both medical and otherwise. In addition, the console 110 can have just one instrument connected to the console 110, and the one instrument can be connected to either port 112 or port 114. The console 110 can also be referred to as a control unit or a main control unit.

What is claimed is:

1. A system for treating tissue, comprising:
    a device comprising:
        a first member, and a second member arranged to move relative to the first member to treat tissue;
    a processor configured to automatically control movement of the second member relative to the first member while the first member remains stationary using position control methodology to compute acceleration and deceleration to move the second member to a next incremental point between points of a position profile in specified periods of time and to enable reversal of direction to return to a starting position, the first and second members cooperatively defining an aperture in the device which depending upon the position of the second member relative to the first member is in fluid communication or is out of fluid communication with a tissue environment; and
    the processor controlling movement of the second member relative to the first member such that there is a hold period at least at some occurrences of the aperture being in fluid communication with the tissue environment, an optimum hold period determined from a function of a suction rate and a length of the second member.

2. The system of claim 1 wherein each point of the position profile corresponds to a position where the aperture of the device is in fluid communication with the tissue environment.

3. The system of claim 1 wherein the second member rotates relative to the first member.

4. The system of claim 1 wherein the second member reciprocates axially relative to the first member.

5. The system of claim 1 wherein the position control methodology uses a stop position of the second member to compute acceleration or deceleration needed to move between points of a position profile.

6. The system of claim 1 wherein the position control methodology uses a point of shaft reversal of the second member to compute acceleration or deceleration needed to move between points of a position profile.

7. A method of treating tissue, comprising:
    providing a device having a first member and a second member arranged to move relative to the first member;
    moving the second member relative to the first member while the first member remains stationary; and
    automatically controlling the movement of the second member using position control methodology to compute acceleration and deceleration to move the second member to a next incremental point between points of a position profile in specified periods of time and to enable reversal of direction to return to a starting position;
    wherein moving the second member relative to the first member alternately places an aspiration opening of the device into fluid communication with or out of fluid communication with a tissue environment;
    wherein the second member is automatically controlled such that there is a hold period at least at some occurrences of the aspiration opening being in fluid communication with the tissue environment, an optimum hold period determined from a function of a suction rate and a length of the second member.

8. The method of claim 7 wherein each point of the position profile corresponds to a position where the aspiration opening of the device is in fluid communication with the tissue environment.

9. The method of claim 7 wherein moving the second member relative to the first member comprises rotating the second member relative to the first member.

10. The method of claim 7 wherein automatically controlling the movement of the second member includes accelerating and decelerating the second member to cause a number of rotations of the second member relative to the first member, and then reversing the direction of rotation of the second member.

11. The method of claim 7 wherein the second member is automatically controlled such that the second member is slowed down or stopped when the aspiration opening is in fluid communication with the tissue environment.

12. The method of claim 7 wherein moving the second member relative to the first member comprises reciprocating the second member axially relative to the first member.

13. The method of claim 7 wherein automatically controlling the movement of the second member using position control methodology includes using a stop position or point of shaft reversal of the second member to compute acceleration or deceleration needed to move between points of a position profile.

* * * * *